United States Patent
Shoudy et al.

(10) Patent No.: US 10,881,353 B2
(45) Date of Patent: Jan. 5, 2021

(54) MACHINE-GUIDED IMAGING TECHNIQUES

(71) Applicant: General Electric Company, Schenectady, NY (US)

(72) Inventors: David Andrew Shoudy, Niskayuna, NY (US); John Eric Tkaczyk, Niskayuna, NY (US); Xin Wang, Concord, MA (US); Heather Chan, Niskayuna, NY (US)

(73) Assignee: GENERAL ELECTRIC COMPANY, Niskayuna, NY (US)

(*) Notice: Subject to any disclaimer, the term of this patent is extended or adjusted under 35 U.S.C. 154(b) by 37 days.

(21) Appl. No.: 16/430,160

(22) Filed: Jun. 3, 2019

(65) Prior Publication Data

US 2020/0375546 A1    Dec. 3, 2020

(51) Int. Cl.
   *G06K 9/00*      (2006.01)
   *A61B 5/00*      (2006.01)
   (Continued)

(52) U.S. Cl.
   CPC .............. *A61B 5/70* (2013.01); *A61B 5/0064* (2013.01); *A61B 5/0077* (2013.01); *G06T 7/37* (2017.01);
   (Continued)

(58) Field of Classification Search
None
See application file for complete search history.

(56) References Cited

U.S. PATENT DOCUMENTS 7,343,189 B2 * 3/2008 Kagermeier ............ A61B 6/08
                                                                  378/20
7,477,763 B2 * 1/2009 Willis .................. A61B 5/0073
                                                               128/922
(Continued)

FOREIGN PATENT DOCUMENTS

CN         104856720 A    *   8/2015
CN         104856720 B        8/2017
(Continued)

OTHER PUBLICATIONS

Motion and Structure from Orthographic Projections, T. S. Huang et al., 0162-8828/89/0500-0536, IEEE, 1989, pp. 536-540 (Year: 1989).*
(Continued)

*Primary Examiner* — Jayesh A Patel
(74) *Attorney, Agent, or Firm* — Fletcher Yoder, P.C.

(57) ABSTRACT

A method includes generating a three-dimensional (3D) surface map associated with a patient from a patient sensor, generating a 3D patient space from the 3D surface map associated with the patient, determining a current pose associated with the patient based on the 3D surface map associated with the patient, comparing the current pose with a desired pose associated with the patient with respect to an imaging system, determining a recommended movement based on the comparison between the current pose and the desired pose, and providing an indication of the recommended movement. The desired pose facilitates imaging of an anatomical feature of the patient by the imaging system and the recommended movement may reposition the patient in the desired pose.

20 Claims, 7 Drawing Sheets

(51) Int. Cl.
*G06T 7/37* (2017.01)
*G06T 7/73* (2017.01)
(52) U.S. Cl.
CPC ...... *G06T 7/75* (2017.01); *G06T 2207/10028* (2013.01); *G06T 2207/30004* (2013.01)

(56) References Cited

U.S. PATENT DOCUMENTS

| | | | | |
|---|---|---|---|---|
| 8,218,847 | B2* | 7/2012 | Averbuch | A61B 5/064 |
| | | | | 382/131 |
| 8,463,006 | B2* | 6/2013 | Prokoski | A61B 5/415 |
| | | | | 382/128 |
| 8,503,745 | B2* | 8/2013 | Simon | A61B 6/547 |
| | | | | 382/128 |
| 8,712,115 | B2* | 4/2014 | Kirchberg | G06F 19/321 |
| | | | | 382/128 |
| 8,880,223 | B2* | 11/2014 | Raj | A61B 90/00 |
| | | | | 700/264 |
| 9,665,936 | B2* | 5/2017 | Kluckner | G06T 11/005 |
| 9,918,701 | B2* | 3/2018 | Hedlund | A61B 6/032 |
| 10,010,379 | B1* | 7/2018 | Gibby | G16H 30/40 |
| 10,635,930 | B2* | 4/2020 | Geiger | G06T 7/73 |
| 2003/0133602 | A1* | 7/2003 | Bani-Hashemi | A61N 5/1049 |
| | | | | 382/131 |
| 2003/0231789 | A1* | 12/2003 | Willis | A61B 5/0422 |
| | | | | 382/128 |
| 2005/0018891 | A1* | 1/2005 | Barfuss | A61B 6/5223 |
| | | | | 382/131 |
| 2005/0089205 | A1* | 4/2005 | Kapur | A61B 8/5238 |
| | | | | 382/128 |
| 2007/0223794 | A1* | 9/2007 | Preiss | G06T 7/33 |
| | | | | 382/128 |
| 2008/0085042 | A1* | 4/2008 | Trofimov | G06T 17/00 |
| | | | | 382/128 |
| 2008/0269588 | A1* | 10/2008 | Csavoy | A61B 90/36 |
| | | | | 600/407 |
| 2008/0317312 | A1* | 12/2008 | Carl | A61B 90/36 |
| | | | | 382/131 |
| 2010/0177163 | A1* | 7/2010 | Yang | G06T 15/503 |
| | | | | 348/45 |
| 2010/0272237 | A1* | 10/2010 | Ein-Gal | A61N 5/1049 |
| | | | | 378/65 |
| 2010/0280365 | A1* | 11/2010 | Higgins | A61B 5/418 |
| | | | | 600/424 |
| 2011/0170752 | A1* | 7/2011 | Martin | G09B 23/285 |
| | | | | 382/128 |
| 2013/0237811 | A1* | 9/2013 | Mihailescu | A61B 8/4438 |
| | | | | 600/424 |
| 2013/0245461 | A1* | 9/2013 | Maier-Hein | A61B 5/742 |
| | | | | 600/476 |
| 2014/0142435 | A1* | 5/2014 | Bernal | A61B 5/091 |
| | | | | 600/476 |
| 2015/0071527 | A1* | 3/2015 | Meir | H04N 13/111 |
| | | | | 382/154 |
| 2016/0157938 | A1* | 6/2016 | Breisacher | G16H 50/50 |
| | | | | 703/11 |
| 2016/0196672 | A1* | 7/2016 | Chertok | G06K 9/4628 |
| | | | | 382/156 |
| 2016/0306924 | A1* | 10/2016 | Singh | G16H 30/20 |
| 2018/0071452 | A1* | 3/2018 | Sharma | G16H 30/40 |
| 2018/0235714 | A1* | 8/2018 | Kuo | A61B 5/0064 |
| 2019/0000564 | A1* | 1/2019 | Navab | G06T 7/521 |
| 2019/0380792 | A1* | 12/2019 | Poltaretskyi | A61B 5/1122 |

FOREIGN PATENT DOCUMENTS

| | | | |
|---|---|---|---|
| WO | 2018015414 A1 | 1/2018 | |
| WO | 2018075053 A1 | 4/2018 | |
| WO | WO-2018075053 A1 * | 4/2018 | .............. G06T 7/70 |

OTHER PUBLICATIONS

Computer assisted 3-D ultrasound probe placement for emergency healthcare applications, Mandi Marsousi et al., IEEE, 10.1109/TII.2016, May 18, 2016, p. 1 (Year: 2016).*
Boulic et al, "An Anatomic Human Body for Motion Capture", EMMSEC '98, Sep. 1998.
Dikmen et al, "Joint detection and localization of multiple anatomical landmarks through learning", Proceedings vol. 6915, Medical Imaging 2008: Computer-Aided Diagnosis, Mar. 17, 2008.
Marsousi et al, "Computer-Assisted 3-D Ultrasound Probe Placement for Emergency Healthcare Applications", IEEE Transactions on Industrial Informatics, vol. 12, Issue 4, Aug. 2016.

* cited by examiner

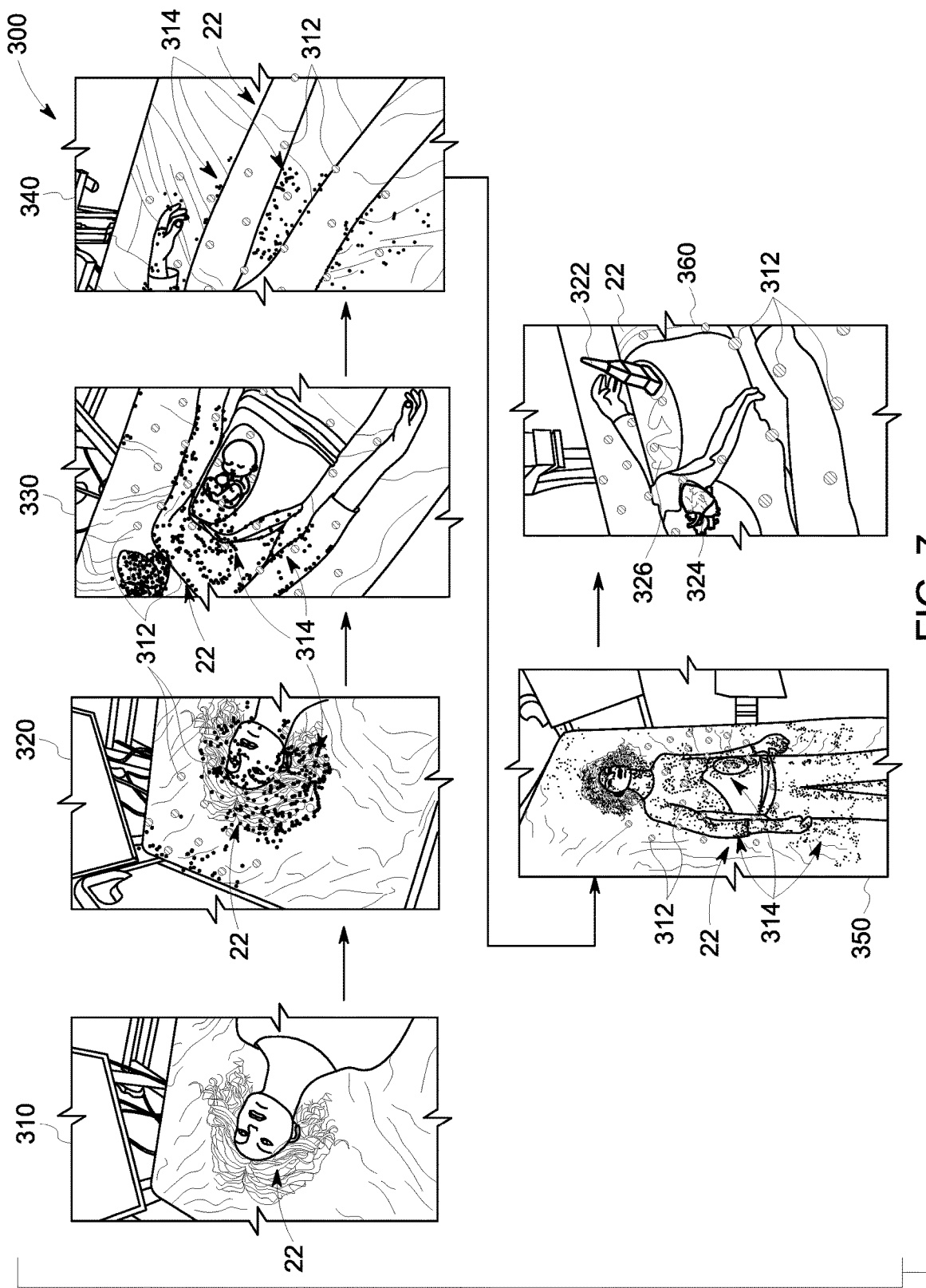

MACHINE-GUIDED IMAGING TECHNIQUES

BACKGROUND

The subject matter disclosed herein relates to medical imaging, and more particularly to systems and methods for guiding medical imaging positioning and alignment.

Proper performance of medical imaging techniques typically involves positioning a patient in an appropriate pose and/or placing an imaging device in an appropriate orientation and/or position based on the particular type of medical imaging technique. Such medical imaging techniques may include ultrasound imaging, magnetic resonance imaging (MRI), computerized tomography (CT), and X-ray imaging. An operator may position the patient in the appropriate pose and/or place the imaging device in an appropriate orientation and position to acquire a desired anatomy or region of interest (e.g., a desired tissue or body region to be imaged) in a desired scan plane. With regard to ultrasound imaging, by viewing real-time images of acquired ultrasound data on a monitor of an ultrasound imaging system, the operator may adjust an ultrasound probe into the appropriate position for imaging the target scan plane of the target region of interest. However, it is recognized that there may be some challenges with such positioning methods. For example, manually finding the appropriate pose of the patient and/or the appropriate position and orientation of the imaging device via viewing displayed images alone may be difficult, time consuming, and result in less accurate positioning, especially for unskilled users.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a medical imaging guidance system may have a patient sensor that may receive three-dimensional (3D) data associated with a patient and an imaging system that has an imaging hardware component that may acquire image data of an anatomical feature associated with the patient. The imaging system may have a hardware position sensor associated with the imaging hardware component. The medical guidance system may also have a processor that generates a 3D surface map associated with the patient based on the 3D data, generates a 3D patient space from the 3D surface map associated with the patient, generates a 3D patient model by mapping an anatomical atlas to the 3D patient space, determines a desired position associated with the imaging hardware component to acquire imaged data of the anatomical feature, determines a current position associated with the imaging hardware component from the hardware position sensor, and determine a desired movement associated with the imaging hardware component to position the imaging hardware component at the desired position. The 3D patient model may have one or more 3D representations of anatomical features of a human body within the 3D patient space.

In another embodiment, a method may include generating a three-dimensional (3D) surface map associated with a patient from a patient sensor, generating a 3D patient space from the 3D surface map associated with the patient, determining a current pose associated with the patient based on the 3D surface map associated with the patient, comparing the current pose with a desired pose associated with the patient with respect to an imaging system, determining a recommended movement based on the comparison between the current pose and the desired pose, and providing an indication of the recommended movement. The desired pose facilitates imaging of an anatomical feature of the patient by the imaging system and the recommended movement may reposition the patient in the desired pose.

In yet another embodiment, a medical imaging guidance system may have a processor that generates a three-dimensional (3D) surface map associated with a patient from a patient sensor, generates a 3D patient space from the 3D surface map associated with the patient, generates a 3D patient model by applying an anatomical atlas to the 3D patient space, and determines a desired position associated with an imaging hardware component of an imaging system that acquires image data of the anatomical feature. The 3D patient model may have one or more 3D representations of anatomical features of a human body within the 3D patient space.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 7 illustrates a series of visualizations presented to the operator via the mobile device of FIG. 6 to assist the operator in positioning an ultrasound probe to acquire the desired scan plane of the desired anatomical feature of the patient, in accordance with aspects of the present disclosure.

DETAILED DESCRIPTION

Figure 1:
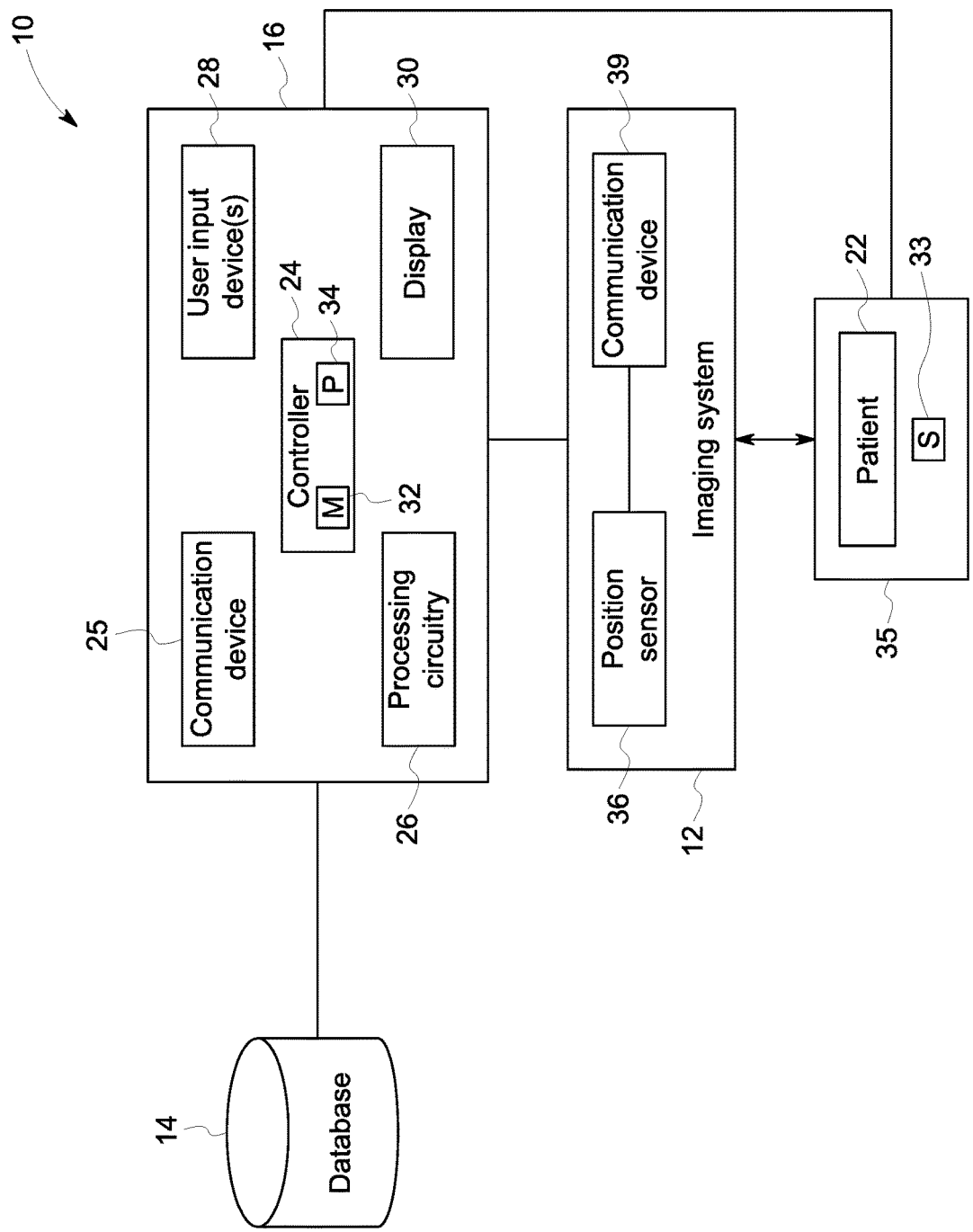
FIG. 1 illustrates a block diagram of an embodiment of a guidance system that may assist an operator in acquiring a desired scan plane of a desired anatomical feature of a patient, in accordance with aspects of the present disclosure.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. One or more specific embodiments of the present embodiments described herein will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As mentioned above, medical imaging systems (e.g., ultrasound, MRI, CT, x-ray) may be operated by skilled technicians trained in positioning a patient in an appropriate pose and/or placing an imaging device in an appropriate position and/or orientation to image a desired region of interest on the patient in a desired scan plane. These technicians may use acquired imaging data for guidance. A challenge in the medical imaging field to widespread growth and adoption of imaging systems in physician's offices and throughout the developing worlds is the lack of skilled technicians or operators capable of performing such interpretation of data and adjusting the pose of the patient and/or position and orientation of the imaging device accordingly. For example, to accurately perform ultrasound imaging of a desired anatomical feature of a patient, an operator must properly align an ultrasound probe of an ultrasound system with the desired anatomy, interpret ultrasound images while controlling settings of the ultrasound system to bring the desired anatomy into view, and navigate the ultrasound probe to identify the appropriate scan planes to store for the examination of the patient. In another example, to accurately perform X-ray imaging of a desired anatomical feature of a patient, an operator must properly position the patient in a particular pose with respect to the X-ray imaging system hardware, interpret an acquired X-ray image to determine whether the desired anatomical features are properly imaged, and adjust the position of the patient or imaging hardware if the desired anatomical features are not properly imaged. The scan plane may be a planar section through the body or a projection of the body onto a plane. Multiple scan planes can direct the acquisition of a volumetric dataset and provide volumetric visualizations of the external and internal body anatomy. The patient space for the X-ray system comprises the alignment of the targeted anatomical feature along the line from the X-ray source to detector such that projection of the feature is completely captured by the active area of the detector. As such, it may be desirable for the medical imaging system to provide guidance to less skilled operators so that such operators may obtain proper medical images for diagnosis without repeating acquisitions or unduly delivering radiation dose. Accordingly, an operator-independent imaging system may automate some operational steps that are typically performed by an operator and provide machine guidance to the operator to perform other operational steps. For example, the operator-independent imaging system may automate many selections of parameters and/or characteristics than an operator would conventionally adjust to perform a particular type of medical imaging of the patient.

Additionally, embodiments of a guidance system are provided herein to provide guided imaging techniques to the operator to acquire one or more desired scan planes of one or more desired anatomical features (e.g., internal or external anatomy) of the patient. For example, based on a respective imaging modality (e.g., ultrasound, MRI, CT, X-ray), the guidance system may provide guidance to the operator to position and/or orient the patient with respect to one or more imaging hardware components associated with an imaging system. In some embodiments, the operator may provide an examination type or prescription as an input for the guidance system. The examination type or prescription, for example, may include data indicative of a desired scan plane to be acquired of a desired anatomical feature of the patient. Based on the data, the guidance system may determine a desired patient position and/or patient orientation with respect to imaging hardware components associated with the imaging system for acquiring the desired scan plane of the desired anatomical feature of the patient. The guidance system may provide guidance to the operator to position the patient in the desired patient position and/or patient orientation. For example, the guidance system may receive patient position and/or orientation data. In some embodiments, the patient position and/or patient orientation data may be acquired in real-time or substantially in real-time. The guidance system may then compare the position and/or orientation of the patient to the desired patient position and/or patient orientation with respect to the imaging hardware components associated with the imaging device. Based on the comparison of the position and/or orientation of the patient with the desired patient position and/or patient orientation, the guidance system may determine a directional movement, an angular movement, or both, to assist the operator in positioning and/or orienting the patient with respect to the imaging hardware components associated with the imaging system to acquire the desired scan plane of the desired anatomical features of the patient. The guidance system may provide guidance to the operator visually, audibly, haptically, or via any other suitable mechanisms to assist the operator in positioning and/or orienting the patient in the desired patient position and/or patient orientation. In some embodiments, the guidance system may provide guidance to the patient directly to allow the patient to self-position in the desired patient position and/or patient orientation, or the imaging system may provide guidance to the operator and the patient.

For some imaging modalities, such as ultrasound imaging and X-ray imaging, the guidance system may determine a desired position and/or orientation of one or more imaging hardware components for acquiring the desired scan plane of the desired anatomical feature of the patient. For example, the imaging hardware components may include an ultrasound probe or detectors. The guidance system may receive position and/or orientation data associated with the image hardware components. In some embodiments, the image hardware position and/or orientation data may be acquired in real-time or substantially real-time. Based on a comparison of the image hardware position and/or orientation data with the desired position and/or orientation of the imaging hardware components, the guidance system may automatically place or facilitate the manual placement of the imaging hardware components. For example, the guidance system may automatically position an x-ray detector in the desired position and/or orientation to acquire the desired scan plane of the desired anatomical feature of the patient. In another example, the guidance system may provide guidance to the operator to move an ultrasound probe to the appropriate position and/or orientation to acquire the desired scan plane of the desired anatomical feature of the patient. The guidance system may determine a directional movement, an angular movement, or both, to assist the operator in positioning and/or orienting the imaging hardware components to acquire the desired scan plane of the desired anatomical features of the patient. The guidance system may provide the guidance to the operator visually, audibly, haptically, or via any other suitable mechanisms to assist the operator in positioning and/or orienting the imaging hardware components in the desired position and/or orientation. In some embodiments, the guidance system may automatically position or facilitate the manual placement of the imaging hardware components before providing guidance to the operator and/or the patient to position the patient in the desired patient position and/or patient orientation. In such embodiments, the desired patient position and/or patient orientation may be determined based on the position and/or orientation of the imaging hardware components as well as the desired scan plane to be acquired of the desired anatomical feature of the patient.

Further, some embodiments of the guidance system provided herein provide guidance to an operator via a three-dimensional (3D) patient model. For example, the 3D patient model may visually present the expected position and/or orientation of anatomical features of the patient to the operator. The guidance system may generate the 3D patient model by generating a 3D surface map of the patient, identifying reference points (e.g., anatomical landmarks) based on the 3D surface map, and deforming an anatomical atlas to the patient space defined by the 3D surface map of the patient. In this way, the guidance system may visually guide the operator in positioning and/or orienting the patient and/or the imaging hardware components in respective positions and/or orientations to acquire the desired scan plane of the desired anatomical feature of the patient.

It should be noted that the guidance system may direct the operator to move (or not move) the patient, or portions thereof, in any combination of directions and/or angles permitted by the degrees of freedom associated with the patient's joints. For example, an upper limb of a human, excluding the hand, has seven degrees of freedom. The shoulder has three degrees of freedom (e.g., shoulder pitch, shoulder roll, arm yaw), the elbow has one degree of freedom (e.g., elbow pitch), and the wrist has three degrees of freedom (e.g., wrist pitch, wrist yaw, and wrist roll). Additionally, it should be noted that the medical imaging system may automatically position or facilitate the manual placement of the imaging hardware components in any combination of directions and/or angles to assist the operator in acquiring the desired scan plane of the desired anatomical features of the patient. For example, the medical imaging system may guide positioning of the imaging hardware components in six degrees-of-freedom (DOF) (i.e., spatial position and angular orientation). Further, although the embodiments described herein relate to directing the operator to position and/or orient the patient and/or the imaging hardware components in respective positions and/or orientations to acquire the desired scan plane of the desired anatomical feature of the patient, it should be noted that such techniques may be adapted and used to direct the operator to position and/or orient the patient for non-imaging procedures and techniques. For example, such non-imaging procedures may include biopsies, venipuncture, or other suitable procedures and techniques.

With the foregoing in mind, FIG. 1 illustrates a block diagram of an embodiment of a guidance system 10 having an imaging system 12 that may be used to acquire one or more desired scan planes of one or more desired anatomical features of a patient 22. For example, the imaging system 12 may include an ultrasound imaging system, an X-ray imaging system, an MRI imaging system, a CT imaging system, or any other suitable imaging modality that may be used to acquire a desired scan plane of a desired anatomical feature of the patient 22. In the illustrated embodiment, the guidance system 10 may include a control unit 16 (e.g., a monitor, a console, or a user interface) which may control operation of the imaging system 12 and process image data received from the imaging system 12. For example, the imaging system 12 may include an ultrasound probe and the control unit 16 may control operation of the ultrasound probe and process image data acquired by the ultrasound probe of the patient 22. The imaging system 12 may be coupled to the control unit 16 via any suitable technique for communicating image data and control signals between the imaging system 12 and the control unit 16, such as a wireless, optical, coaxial, or other suitable connection.

The imaging system 12 is communicatively coupled to the control unit 16 of the guidance system 10 to facilitate image collection and processing. As will be appreciated, the control unit 16 may include a number of elements to control operation of the imaging system 12, facilitate automatic positioning or manual placement of one or more image hardware components of the imaging system 12, facilitate positioning or orienting of the patient in a particular pose with respect to the image hardware components of the imaging system 12, and facilitate production of images based on imaging data received from the imaging system 12. For instance, as illustrated, the control unit 16 may include a controller 24, processing circuitry 26, one or more user input devices 28, and a display 30.

The controller 24 may include a memory 32 and a processor 34. In some embodiments, the memory 32 may include one or more tangible, non-transitory, computer-readable media that store instructions executable by the processor 34 and/or data to be processed by the processor 34. For example, the memory 32 may include random access memory (RAM), read only memory (ROM), rewritable non-volatile memory such as flash memory, hard drives, optical discs, and/or the like. Additionally, the processor may include one or more general purpose microprocessors, one or more application specific processors (ASICs), one or more field programmable logic arrays (FPGAs), or any combination thereof. The controller 24 may control the imaging system 12 to acquire imaging data associated with the patient 22. In some embodiments, the imaging data may include two-dimensional (2D) imaging data, one or more planes of imaging data built into a volume of imaging data, a volume of imaging data, or any other data representative of an anatomical feature. Additionally, the controller 24 may be part of the guidance system 10 and control other elements of the guidance system 10 to provide guided medical imaging techniques to an operator of the guidance system 10 to acquire the desired scan planes of the desired anatomical features of the patient 22, as discussed in greater detail below.

The processing circuitry 26 may include receiving and conversion circuitry. The processing circuitry 26 may receive electrical signal data from the imaging system 12 indicative of imaging data associated with the patient 22. The processing circuitry 26 may process the received electrical signal data, such as correcting for noise artifacts, or the like. The processing circuitry 26 may then convert the electrical signal data into an image (e.g., an ultrasound image, a tomography scan, an x-ray, or an MRI) for presentation via the display 30. The controller 24 may then cause display of the image or images produced by the processing circuitry 26 from the electric signal data received from the imaging system 10.

The controller 24 may also include a communication device 25 that enables the control unit 16 to communicate data between the control unit 16 and the imaging system 12. For example, in the illustrated embodiment, the imaging system 12 may have a communication device 39 that includes a network interface that may enable the imaging system 12 to communicate via various protocols such as various wired or wireless communication protocols, such as Wi-Fi, mobile telecommunications technology (e.g., 2G, 3G, 4G, or LTE), Bluetooth®, near-field-communications technology, and the like.

The illustrated embodiment depicts the control unit 16 and the imaging system 12 as separate components that are communicably coupled to one another. In such embodiments, the imaging system 12 may, for example, process acquired image data and generate two-dimensional images that may be communicated to the control unit 16, and the control unit 16 may, for example, process the received two-dimensional images and generate three-dimensional volumes of the image data. In other embodiments, the control unit 16 and the imaging system 12 may be a single device.

In operation, the controller 24 may receive a signal (e.g., a user selection or a user input) indicative of a desired anatomical feature of the patient 22 and/or a desired scan plane of the desired anatomical feature via the one or more user input devices 28 of the control unit 16. The one or more user input devices 28 may include a keyboard, a touchscreen, a mouse, buttons, switches, or other devices suitable to allow the operator to input the desired anatomical feature and/or the desired scan plane of the desired anatomical feature.

The controller 24 may determine the desired anatomical feature of the patient 22 and/or the desired scan plane of the desired anatomical feature based on the signal. Based on the desired anatomical feature and/or the desired scan plane, the controller 24 may then determine a desired patient position and/or orientation with respect to one or more imaging hardware components of the imaging system 12 to acquire imaging data of the desired anatomical feature of the patient 22 and/or the desired scan plane of the desired anatomical feature. In some embodiments, the desired patient position and/or orientation is the optimal position and/or orientation of the patient to acquire imaging data of the desired anatomical feature and/or the desired scan plane of the desired anatomical feature. The controller 24 may then provide guidance to the operator of the imaging system 12 to position and/or orient the patient 22 in the desired patient position and/or orientation.

In some embodiments, the controller 24 may direct the operator to move (or not move) the patient 22, or portions thereof, in a combination of directions and/or angles to position the patient 22 in the desired patient position and/or orientation with respect to the imaging hardware components of the imaging system 12. For example, the controller 24 may determine one or more directional movements, one or more angular movements, or both, associated with the patient 22 and/or portions of the patient's limbs, torso, or head to position the patient 22 in the desired patient positon and/or orientation. Additionally, or alternatively, the controller 24 may determine the directional movements, the angular movements, or both, associated with the patient 22 based on based on anatomical and/or physiological information associated with the patient 22. The controller 24 may receive the anatomical or physiological information associated with the patient 22 from the database 14 and/or via the user input devices 28.

In some embodiments, the anatomical and/or physiological information associated with patient 22 may include the degrees of freedom associated with the desired anatomical feature to be imaged or any surrounding and/or adjacent anatomical features of the patient 22. For example, an upper limb of a human, excluding the hand, has seven degrees of freedom. The shoulder has three degrees of freedom (e.g., shoulder pitch, shoulder roll, arm yaw), the elbow has one degree of freedom (e.g., elbow pitch), and the wrist has three degrees of freedom (e.g., wrist pitch, wrist yaw, and wrist roll). The controller 24 may determine the directional movements, the angular movements, or both, associated with the patient 22 based on the degrees of freedom permitted by certain joints of the patient 22 that may be subjected to the movements determined by the controller 24 to position and/or orient the patient 22 in the desired position and/or orientation. In some embodiments, the anatomical information may include the medical history of the patient, such as a history of diseases, traumas, or other physical ailments suffered by the patient. In such embodiments, the guidance provided by the controller 24 may be based on such information to prevent or minimize movements of the patient 22, or portions thereof, that may aggravate pre-existing conditions suffered by the patient 22.

In some embodiments, the anatomical information and/or physiological information may include one or more anatomical models. For example, the anatomical models may be associated with anatomical features such a body part, an organ, a muscle, a bone, or the like. The anatomical models may include a polygonal or volumetric 3D model of the anatomical feature. The anatomical model may also be associated with an indexed list of anatomical components of the anatomical feature. The indexed list of anatomical components may include each body part, organ, muscle, bone, or the like, that is connected with each other body part, organ, muscle, bone, or the like, in the associated anatomical feature. Each anatomical component in the indexed list may share at least one point of correspondence to another anatomical component in the indexed list. For example, with respect to the anatomical feature of the hip-to-femur joint, the anatomical components may include the last lumbar vertebrae (L5), the sacrum (S1), the ilium, the ischium, and the femur. As such, each anatomical model may define the linkages between each of the anatomical components associated with each anatomical model. For example, in the 3D model of the anatomical feature, a point of correspondence for the femur 'A' and the point of correspondence for the ischium 'B' may be coincident but allow a limited range of relative orientation for the femur and the ischium. This range may be quantified by a Rodrigues vector, Euler angles, Quaternions, and the like. Thus, each anatomical component may have a particular orientation relative to each other, and the particular orientation of each anatomical component may be associated with a respective range of relative orientation with respect to another anatomical component. For example, the ischium has an orientation 'm' and the femur has an orientation 'n'. A relative orientation 'm–n' exists between the ischium and the femur. The relative orientation 'm–n' may be implemented as an inverse and a product of quaternions in a quaternion representation of the orientation. Accordingly, the controller 24 may receive such anatomical models and/or indexes of anatomical components from the database 14. The controller 24 may determine the directional movements, the angular movements, or both, associated with the patient 22 based on the received anatomical models and/or indexes to position and/or orient the patient 22 in the desired position and/or orientation.

Additionally, or alternatively, the controller 24 may determine a desired position and/or orientation of one or more imaging hardware components of the imaging system 12 to acquire the imaging data based on the desired anatomical feature and/or the desired scan plane. For example, the imaging hardware components may include an ultrasound probe or one or more detectors. In some embodiments, the desired position and/or orientation of respective imaging hardware components may be the optimal position and/or orientation of the respective imaging hardware components to acquire imaging data of the desired anatomical feature and/or the desired scan plane of the desired anatomical feature. The imaging system 12 may include one or more position sensors 36 for detecting the position and/or orientation of respective imaging hardware components of imaging system 12. The position sensor 36 may be disposed about a respective imaging hardware component and may be a position sensor, an orientation sensor, such as a gyroscope, an inertial measurement unit, electromagnetic tracking, optical tracking, or any other suitable sensor that may allow for detection of a current position and/or orientation of the imaging hardware component. The position sensor 36 may be communicatively coupled to the controller 24 via a wired or wireless connection and may send one or more signals to the controller 24 indicative of the current position and/or orientation of the imaging hardware component.

The controller 24 may facilitate automatic movement or manual placement of the imaging hardware components in any combination of directions and/or angles to assist the operator in acquiring the desired scan plane of the desired anatomical features of the patient 22. For example, the controller 24 may guide positioning of the imaging hardware components in six degrees-of-freedom (i.e., spatial position and angular orientation). The controller 24 may compare the current position and/or orientation of the imaging hardware components, based at least in part on respective signals received from the position sensor 36 of the imaging system 12, to the desired position and/or orientation of the imaging hardware components. Based on the comparison, the controller 24 may determine whether the imaging hardware components are in the desired position and/or orientation to sufficiently image the desired anatomical features in the desired scan plane. If the controller 24 determines that the imaging hardware components are not in the desired position and/or orientation, the controller 24 may facilitate automatic movement or manual placement of the imaging hardware components in the desired position and/or orientation. For example, the controller 24 may send one or more command signals to one or more actuators that automatically positions a detector in the desired position and/or orientation. In another example, the controller 24 may provide guidance to the operator to manually place the imaging hardware components in the desired position and/or orientation.

In some embodiments, the controller 24 may receive a signal (e.g., a user selection or a user input) indicative of an examination type associated with the patient 22 via the user input devices 28 or from one or more databases 14 communicatively coupled to the control unit 16. For example, the database 14 may include one or more scheduled examinations that are associated with one or more patients 22. In such embodiments, the examination type may include a numerical string indicative of the examination type, an alpha-numerical string indicative of the examination type, or a description of the examination type. The examination type may be indicative of one or more desired anatomical features of the patient 22 and/or one or more desired scan planes of the desired anatomical features of the patient 22. For example, the examination type may include data representative of a body part, a preliminary diagnosis of the patient 22, an imaging modality, or the like. As such, the controller 24 may determine the desired anatomical features of the patient 22 and/or the desired scan planes of the desired anatomical features based on the received examination type.

The controller 24 may determine that the patient 22 is in an appropriate position and/or orientation (e.g., a desired position and/or orientation) to sufficiently image the desired anatomical feature and/or the desired scan plane of the desired anatomical feature. In some embodiments, the guidance system 10 may include sensing mechanisms to detect the location of the patient 22 and to determine the position and/or orientation of imaging hardware components associated with the imaging system 12 with respect to the patient 22. That is, the guidance system 10 may include one or more patient position and/or orientation sensors 33, such as weight sensors, contact sensors, cameras, range or depth cameras, stereo cameras, a radar or laser scanning system, or other suitable sensing mechanisms, disposed about the imaging space 35 of the imaging system 12 in which the patient 22 is positioned during imaging, or at any other suitable position about the imaging system 12 suitable for detecting the position of the patient 22. In some embodiments, the patient position and/or orientation sensors 33 may be in a fixed position in the imaging space 35 of the imaging system 12 or may be mobile (e.g., as part of a mobile device). The patient position and/or orientation sensor 33 may be communicatively coupled to the controller 24 via a wired or wireless connection and may send one or more signals to the controller 24 indicative of the position and/or orientation of the patient 22 about the imaging space 35. In some embodiments, the imaging hardware components may have one or more position and/or orientation sensors for detecting the position of the patient 22.

Based at least in part on the signals received from the patient position sensor 33 and/or certain patient characteristics, such as height, weight, gender, ethnicity, or the like, of the patient 22, the controller 24 may generate a three-dimensional (3D) patient model (e.g., an anatomical twin) associated with the patient 22 and provide visual guidance to the operator to position and/or orient the patient 22, the imaging hardware components, or both, via the 3D patient model. For example, after generating the 3D patient model, the controller 24 may send a command signal to the display 30 to present the 3D patient model associated with the patient 22 to the operator. The 3D patient model may visually present the expected position and/or orientation of anatomical features of the patient 22 to the operator. In some embodiments, the controller 24 may overlay the 3D patient model over an image or a video of the patient 22 displayed to the operator. In this way, the operator may acquire spatial awareness of the desired anatomical feature and/or the patient's anatomy adjacent to or surrounding the desired anatomical feature, thereby facilitating proper imaging of the desired anatomical feature.

The controller 24 may generate the 3D patient model by generating a 3D surface map of the patient 22 and the patient's environment (e.g., a bed or a chair), identifying reference points (e.g., anatomical landmarks) within the 3D surface map, and deforming an anatomical atlas to the patient space defined by the 3D surface map of the patient 22 and/or the patient's environment. The controller 24 may receive sensor data and generate a 3D surface map associated with the patient 22 and the patient's environment via the imaging system 12 and/or the patient position and/or orientation sensors 33. Sensor data may include video camera streams, point-cloud distance maps, inertial motion temporal sequence, or any combination thereof. Devices with a point-cloud depth (D) channel in addition to color channels (RGB) can also be used as input to generate a 3D surface map. For example, patient position and/or orientation sensors 33 may include an RGB-D camera, a stereo RGB or RGB-D camera (e.g., mounted above the patient 22), an RBG or RGB-D camera integrated in a mobile device (e.g., a smartphone or a tablet), a radar scanning system, a laser scanning system, or the like. In one embodiment, the RGB-D camera or the stereo RGB-D camera may generate a 3D point cloud of the patient 22 and/or the patient's environment. That cloud can be interpolated or smoothed to generate the 3D surface map. In another embodiment, the RGB or RGB-D camera that is integrated in a mobile device may be used to acquire image data from different viewpoints of the body of the patient 22. The camera may be swept or panned across the body of the patient 22, and techniques such as structure from motion and/or visual-inertial odometry may be used to localize the mobile device in the 3D imaging space 35 and generate 3D surface maps from the sequence of localized camera images. In yet another embodiment, a 3D surface map can be inferred by analysis of a single, motionless camera using algorithms leveraging machine learning that leverage many past data labeled datasets where single camera views are paired with ground truth 3D surface map results. The deep learning technique called "Deep Pose" wraps a surface model around the persons in a camera image. In yet another embodiment, the patient position sensor 33 may include an ultrasound probe with integrated position tracking. For example, the operator may follow a procedure while using the ultrasound probe with integrated position tracking to place the probe on anatomical reference points or drag the ultrasound probe across the surface of the patient 22 (e.g., over one or more predefined reference points or along predefined or random trajectories) to acquire a set of 3D surface points. The guidance system 10 may then extract 3D surface data from the acquired 3D surface points received from the integrated position tracking in the probe. In yet another embodiment, a radar scanning system, a laser scanning system, or any suitable system that emits and detects radio frequency (RF) field distortions may acquire 3D surface data of the patient 22. In yet another embodiment, structure from motion techniques may also be used to generate 3D surface maps from a sequence of camera images. In yet another embodiment, the imaging hardware components may have one or more position and/or orientation sensors for detecting the position of the patient 22. For example, an operator may hold an ultrasound probe or another suitable imaging hardware component within a particular distance from the patient 22 to acquire sensor data of the patient 22 via a camera in the ultrasound probe. The operator may move the ultrasound probe to one or more reference points within a region defined by the distance from the patient 22 to acquire a set of 3D surface points. The guidance system 10 may then extract 3D surface data from the acquired 3D surface points received from the ultrasound probe (e.g., integrated position tracking in the probe).

In any case, based on the acquired sensor data of the patient 22 and/or the patient's environment, the controller 24 may estimate the pose (e.g., the position and/or orientation) of the patient 22 and identify one or more anatomical reference points. For example, the anatomical reference points may include the shoulders, the hips, the knees, or any other suitable anatomical landmark. In some embodiments, the anatomical reference points may be inferred based on the 3D surface map of the patient. The controller 24 may then fuse the anatomical reference points with the acquired 3D surface map of the patient 22 and the patient's environment to generate a 3D surface map of the patient 22 and the patient's environment. The controller 24 may apply image segmentation to the 3D surface map of the patient 22 to separate the 3D surface map of the patient 22 from the 3D surface map of the patient's environment. Based on 3D surface map of the patient 22, the controller 24 may identify or extract 3D anatomical reference points. The controller 24 may then deform one or more anatomical features from an anatomical atlas to the 3D surface map of the patient 22 based on the extracted 3D anatomical reference points to generate the 3D patient model. For example, the controller 24 may apply a rigid, affine, or deformable transformation to register the anatomical atlas with the 3D patient map. In this way, the guidance system 10 may provide the operator with spatial awareness of expected anatomical features via the 3D patient model as the operator positions and/or orients the patient 22 and/or the imaging hardware components in respective positions and/or orientations to acquire the desired scan plane of the desired anatomical feature of the patient 22.

The controller 24 may cause automatic storage in the memory 32 of the image data acquired via the imaging system 12 once the controller 24 has determined that the image hardware components are in the desired position and/or orientation. For example, once the operator has positioned the ultrasound probe in the desired position and/or orientation and the patient 22 is in the desired patient position and/or orientation to sufficiently acquire image data of the desired anatomical feature and/or the desired scan plane of the desired anatomical feature, the controller 24 may automatically cause storage of acquired ultrasound image data. Additionally, or alternatively, the controller may cause automatic storage of 3D surface map acquired via the patient position and/or orientation sensors 33 and/or the generated 3D patient model.

Figure 2:
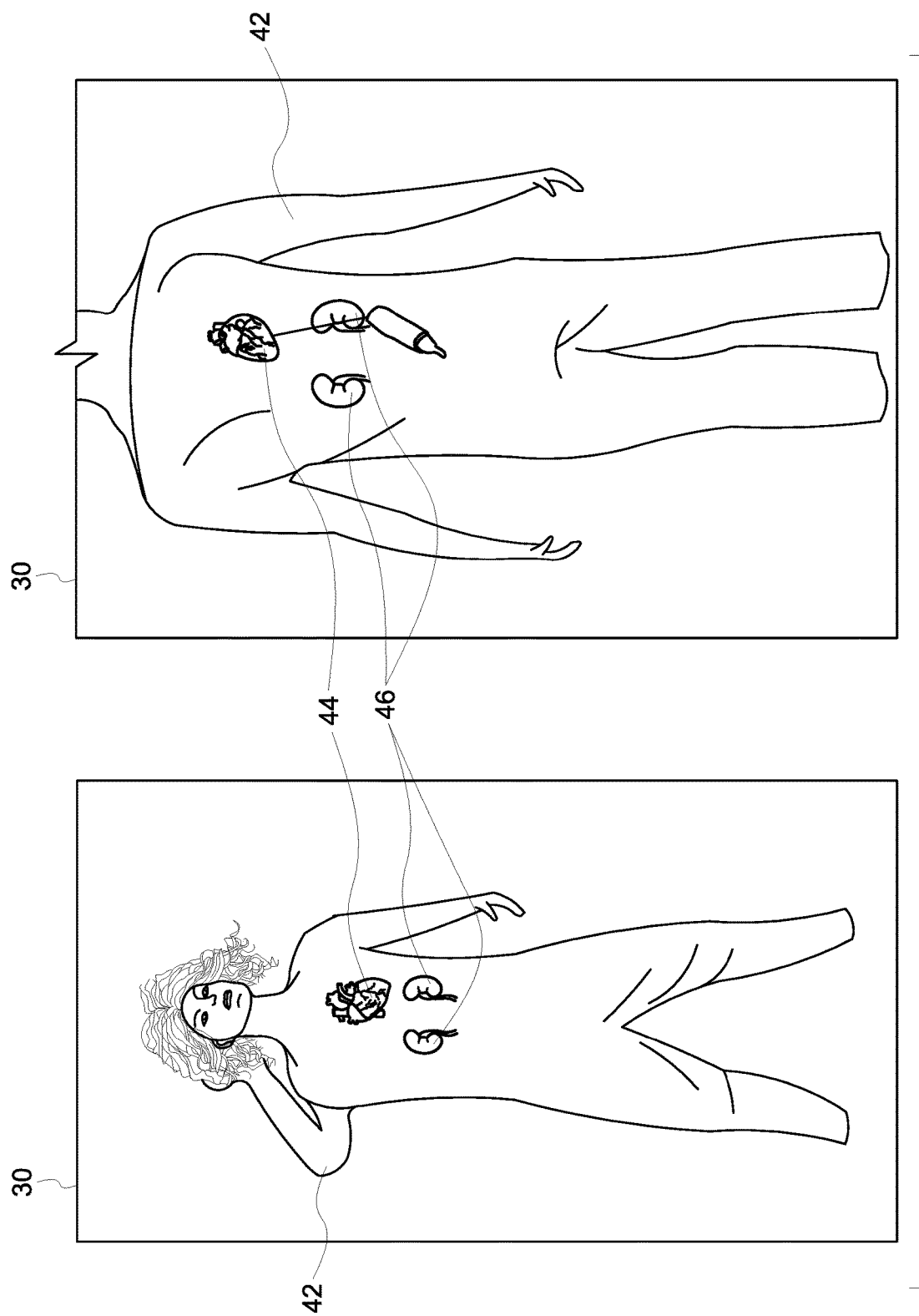
FIG. 2 illustrates an exemplary embodiment of a three-dimensional (3D) patient model that presents the expected positions of one or more anatomical features to the operator of FIG. 1, in accordance with aspects of the present disclosure.

With the foregoing in mind, the guidance system 10 may provide the operator with guidance for positioning the patient 22 in a desired pose (e.g., a desired position and/or orientation) to acquire image data of the desired anatomical feature and/or the desired scan plane of the desired anatomical feature. The guidance provided by the guidance system 10 may be presented to the operator visually. For example, the controller 24 of the guidance system 10 may present one or more graphical visualizations (e.g., the 3D patient model) via the display 30 that direct the operator to position the patient 22 in the desired position and/or orientation. Additionally, the guidance system 10 may facilitate manual positioning of imaging hardware components to acquire image data of the desired anatomical feature and/or the desired scan plane of the desired anatomical feature of the patient 22. With the foregoing in mind, FIG. 2 illustrates an embodiment of the 3D patient model 42 generated by the controller 24 and output via the display 30. The controller 24 may map the 3D patient model 42 to one or more anatomical reference points indicative of the patient's current position and/or orientation. For example, as the patient moves (e.g., lifts an arm, stands up, sits down), the visualization of the 3D patient model 42 may adjust accordingly. As illustrated in the embodiment, the 3D patient model 42 includes an expected position of the heart 44 and an expected position of the kidneys 46. However, in other embodiments, the 3D patient model 42 may include additional or fewer anatomical features to be viewed by the operator. Additionally, in such embodiments in which the imaging system 12 includes ultrasound imaging, the position and/or orientation of the ultrasound probe 48 may be tracked based on one or more position and/or orientation sensors 36 of the ultrasound probe 48. The controller 24 may display the position and/or orientation of the ultrasound probe 48 in real-time or in substantially real-time via the display 30. For example, as illustrated in FIG. 2, the position and/or orientation of the ultrasound probe 48 may be displayed concurrently with the 3D patient model 42. The position and/or orientation of the ultrasound probe 48 may be displayed upon the 3D patient model 42 such that the operator may determine the position and/or orientation of the ultrasound probe 48 with respect to the internal anatomy of the patient 22. Although the ultrasound probe 48 is illustrated as a solid graphic in FIG. 2, it should be noted that the position and/or orientation of the ultrasound probe 48 may be presented in any suitable manner to convey the position and/or orientation of the ultrasound probe 48 with respect to the expected anatomy of the patient 22. For example, the ultrasound probe 48 may be semi-transparent such that the operator 48 may see the boundaries of the ultrasound probe 48 and the orientation of the ultrasound probe 48 but also see any expected anatomical features underneath the ultrasound probe 48.

As mentioned above, the controller 24 may facilitate manual placement of imaging hardware components to assist the operator in acquiring the desired scan plane of the desired anatomical feature of the patient 22. As illustrated in FIG. 2, the controller 24 may present a visual representation of the desired position and/or orientation of the ultrasound probe 48 via the display 30. For example, the controller 24 may present a graphic 50 that represents the angular movements, the directional movements, or both, that the operator should perform with respect to moving the ultrasound probe 48 to the desired position and/or orientation. In the illustrated embodiment, the graphic 50 includes a guideline between the current position of the ultrasound probe 48 and the desired position of the ultrasound probe 48. As the operator moves the ultrasound probe 48 toward or away from the desired position, the controller 24 may determine additional angular movements, additional directional movements, or both, to assist the operator in moving the ultrasound probe 48 from the current position to the desired position. That is, the display 30 of the graphic 50 (and the visualization of the 3D model 42) may update based on a movement of the ultrasound probe in any direction or angle. In other embodiments, the graphic 50 may include a solid or a transparent bounded representation of the desired position and/or orientation of the ultrasound probe 48. For example, the operator may position and/or orient the ultrasound probe 48 such that the position and/or orientation of the ultrasound probe 48 aligns with the bounded representation of the ultrasound probe 48.

Figure 3:
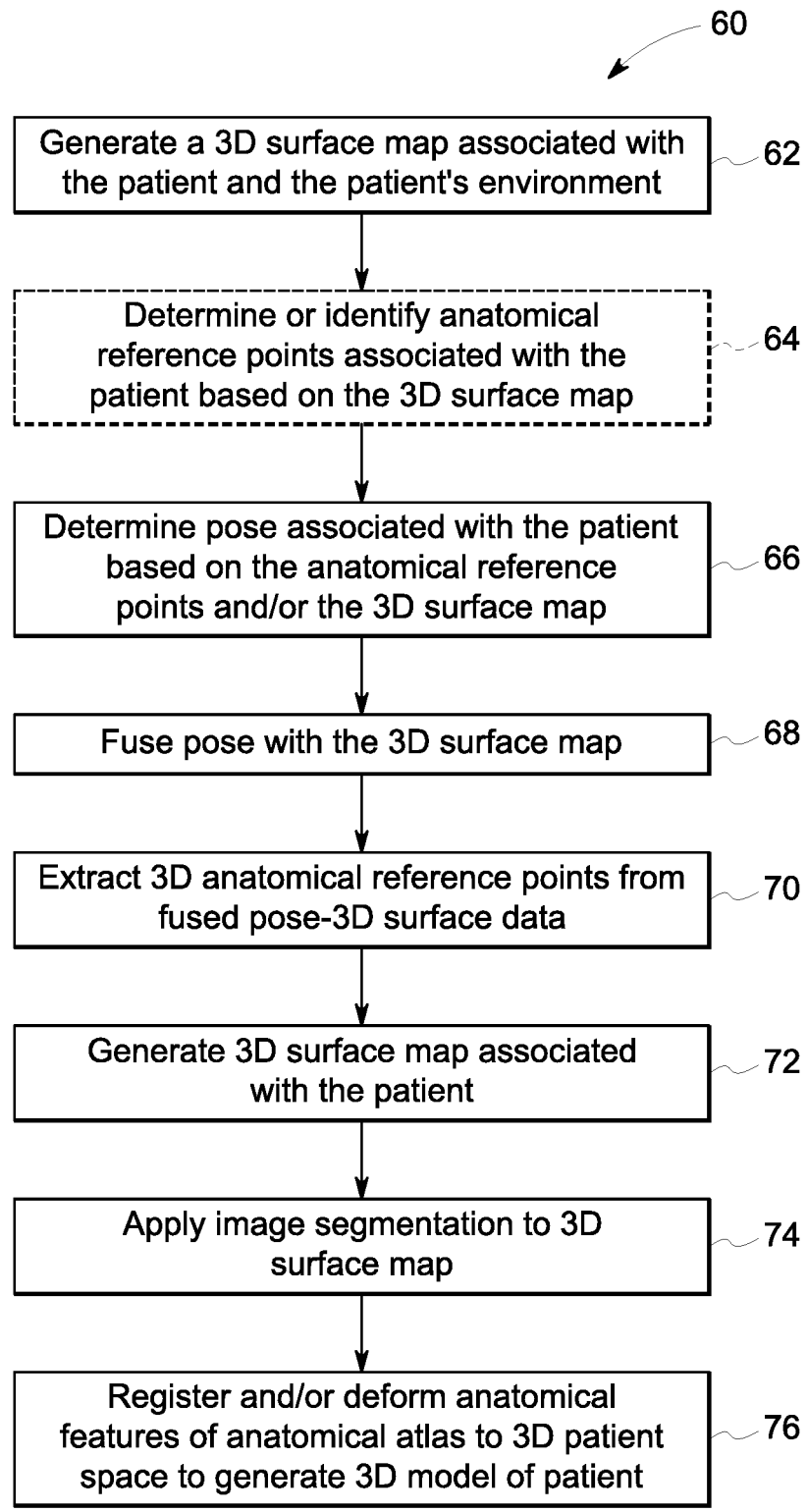
FIG. 3 is a flow chart of a method for generating the 3D patient model of FIG. 2 for display to the operator, in accordance with aspects of the present disclosure.

FIG. 3 illustrates a flow chart of a method 60 for generating the 3D patient model 42 for display to the operator. Although the following description of the method 60 is described in a particular order, it should be noted that the method 60 is not limited to the depicted order, and instead, the method 60 may be performed in any suitable order. Moreover, although the method 60 is described as being performed by the controller 24, it should be noted that it may be performed by any suitable computing device communicatively coupled to the controller 24.

Referring now to FIG. 3, at block 62, the controller 24 of the guidance system 10 may generate a 3D surface map associated with the patient 22 and the patient's environment (e.g., a bed or a chair) via the imaging system 12, the patient position and/or orientation sensors 33, or both. As described above, the imaging system 12 may include an ultrasound imaging system, an MRI, a CT scanner, an x-ray imaging system, or the like, and the patient and/or orientation sensors 33 may include an RGB-D camera, a stereo RGB-D camera (e.g., mounted above the patient 22), an RGB or RGB-D camera integrated in a mobile device (e.g., a smartphone or a tablet), a depth-sensing camera, a radar scanning system, a laser scanning system, or the like. The imaging system 12 may generate the 3D surface map associated with the patient 22 and the patient's environment based on sensor data associated with the patient 22 and the patient's environment. At block 64, the controller 24 may optionally determine or identify one or more anatomical reference points based on the received sensor data and/or the 3D surface map. For example, the anatomical reference points may include the shoulders, the hips, the knees, or any other suitable anatomical landmark. In some embodiments, the anatomical reference points include 2D points identified from 2D images generated from the 3D surface map, an RGB camera, or other suitable imaging data associated with the patient 22. At block 66, the controller 24 may estimate the pose (e.g., the position and/or orientation) of the patient 22 based on the anatomical reference points and/or the 3D surface map. For example, the controller 24 may estimate the pose of the patient 22 using various keypoint techniques, mesh-based techniques, deep-learning techniques, or other suitable pose-estimation or pose-determination techniques.

At block 68, the controller 24 may then fuse the pose of the patient 22 with the 3D surface map of the patient 22 and the patient's environment received at block 62. For example, the pose may be represented by adjoining anatomical reference points determined at block 64. In some embodiments, the adjoining anatomical reference points may include a set of predefined reference points. For example, the set of predefined reference points may include one or more points representing the approximate position or the approximate center of mass of the head, the neck, the shoulders, the elbows, the wrists, the chest, the hips, the knees, the ankles, and/or the like. The controller 24 may fuse the adjoined anatomical reference points to the 3D surface map of the patient 22 and the patient's environment received at block 62. At block 70, the controller 24 may extract one or more 3D anatomical reference points from the fused 3D surface map. In one embodiment, the 3D anatomical reference points may be inferred or extracted directly from a 2D depth image of the patient 22 or a segmented 3D patient surface.

At block 72, the controller 24 may generate a 3D surface map associated with the patient based on the fused 3D surface map at block 70. The controller 24 may apply image segmentation to the fused 3D surface map of the patient 22 and the patient's environment to separate the 3D patient surface map from the 3D environment surface map. The controller 24 may then filter the resulting segmentation to extract the largest connected area representing the 3D patient surface map. For example, the largest connected area may include the 3D anatomical reference points extracted at block 70. It should be understood that filtering the resulting segmentation to extract the largest connected area is a non-limiting example and that other segmentation methods may be used.

In some embodiments, the controller 24 may determine whether the patient 22 is in the desired pose (e.g., the position and/or orientation) or not with respect to the image hardware components of the imaging system 12 based on extracted 3D anatomical reference points and/or deep learning techniques. For example, if the patient 22 is not in the desired pose, the controller 24 may direct the operator to move (or not move) the patient 22, or portions thereof, in a combination of directions and/or angles to position the patient 22 in the desired pose (e.g., the desired patient position and/or orientation) with respect to the imaging hardware components of the imaging system 12. Additional details with regard to repositioning the patient 22 in the desired pose is discussed below with reference to FIG. 4.

After the 3D anatomical reference points and the 3D patient surface map have been extracted, at block 74, the controller 24 may register and deform one or more 3D representations of anatomical features from an anatomical atlas (e.g., a human body atlas) to a patient space defined by the 3D patient surface map to generate the 3D patient model 42 (e.g., an anatomical twin associated with the patient 22) at block 76. For example, the 3D representations of the anatomical features may include one or more organs, bones, muscles, veins, arteries, or other suitable anatomical features to provide the operator with spatial awareness of the expected positons of such features in the 3D patient model 42. In some embodiments, the controller 24 may perform a piecewise deformation of the 3D representations of the anatomical features from the anatomical atlas to the patient space to generate the 3D patient model 42. In this way, the desired anatomical features to be displayed with the 3D patient model 42 may be positioned within the 3D patient model 42 with an increased accuracy.

In some embodiments, the anatomical atlas may be statistically built and updated, such as using machine learning data-analytic techniques, during the operation of a respective imaging system and similar imaging systems at other locations (e.g., within a clinic, geographic region, and/or throughout the world. The anatomical atlas may then be stored in the database 14 and accessed by the controller 24. For example, the database 14 may include one or more anatomical atlases that represent various types of people with respective characteristics (e.g., body type, height, weight, gender, age, or race). The controller 24 may retrieve the anatomical atlas that most closely corresponds to the particular set of characteristics of the patient 22 being imaged. Additionally, previously acquired imaging data associated with the patient 22 may be fused with the anatomical atlas and provide patient-specific anatomical data that may be registered and deformed to the patient pose to generate the 3D patient model 42. That is, the previously acquired imaging data associated with the patient 22 may provide the estimated positions of anatomical features in the 3D patient model 42 with an increased accuracy as well as more appropriately visualize the internal anatomy of the patient 22.

Figure 4:
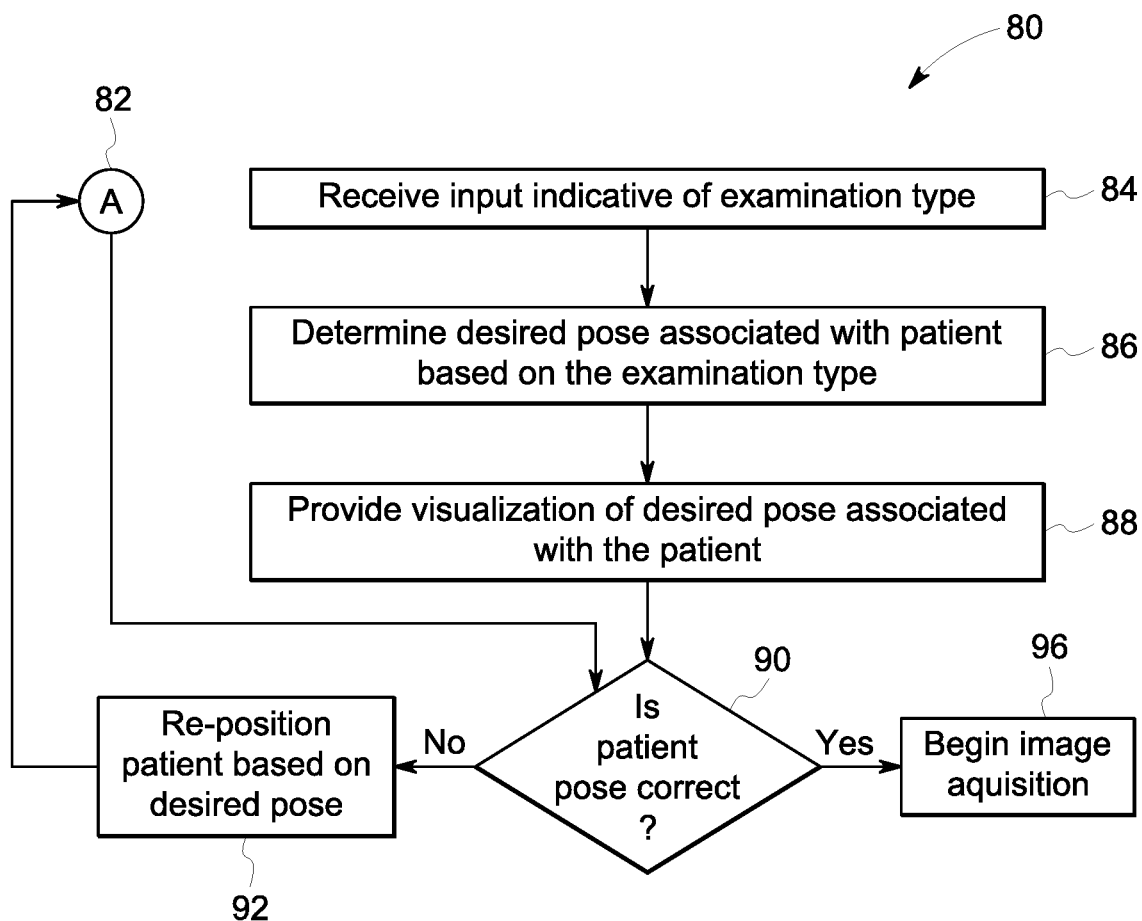
FIG. 4 is a flow chart of a method for validating 3D patient surface map utilized for generating the 3D patient model of FIG. 2, in accordance with aspects of the present disclosure.

As mentioned above, the controller 24 may determine whether the patient 22 is in the desired pose (e.g., the position and/or orientation) or not with respect to the image hardware components of the imaging system 12 based on 3D anatomical reference points and/or deep learning techniques. For example, if the patient 22 is not in the desired pose, the controller 24 may direct the operator to move (or not move) the patient 22, or portions thereof, in a combination of directions and/or angles to position the patient 22 in the desired pose (e.g., the desired patient position and/or orientation) with respect to the imaging hardware components of the imaging system 12. With the foregoing in mind, FIG. 4 illustrates a flow chart of a method 80 for positioning the patient 22 in a desired pose based on a comparison between the current pose of the patient 22, as indicated by the 3D patient surface map extracted at block 72, and the desired pose. Although the following description of the method 80 is described in a particular order, it should be noted that the method 80 is not limited to the depicted order, and instead, the method 80 may be performed in any suitable order. For example, although block 82 is shown as being performed parallel with blocks 84-88, the performance of block 82 may be performed before, after, or at any other suitable time with respect to blocks 84-88. Moreover, although the method 80 is described as being performed by the controller 24, it should be noted that it may be performed by any suitable computing device communicatively coupled to the controller 24.

Referring now to the FIG. 4, at block 82, the controller 24 may perform the method 60 of FIG. 3 at blocks 62 to 76, or any suitable combination thereof. That is, the controller 24 may generate a 3D surface map associated with the patient 22 and the patient's environment and generate a 3D patient model associated with the patient 22 based on the 3D surface map of the patient 22, a pose of the patient 22, and an anatomical atlas. In some embodiments, the controller 24 may display the 3D surface map and/or the 3D patient model of the patient 22 via the display 30 such that the operator and/or the patient 22 may view the position and/or orientation of the patient 22 with respect to the imaging hardware components of the imaging system 12.

At block 84, the operator and/or the patient 22 may provide an examination type as an input for the controller 24 of the guidance system 10. For example, the controller 24 may receive a signal (e.g., a user selection or a user input) indicative of the examination type associated with the patient 22 via one or more user input devices 28 or a database 14 communicatively coupled to the control unit 16. The examination type may include data indicative of one or more desired anatomical features of the patient 22 to be imaged or one or more desired scan planes to be acquired of the desired anatomical features of the patient 22. For example, the examination type may include data representative of a body part, a preliminary diagnosis of the patient 22, an imaging modality, or the like. In some embodiments, the examination type may include a numerical string indicative of the examination type, an alpha-numerical string indicative of the examination type, or a description of the examination type.

At block 86, the controller 24 may determine a desired pose (e.g., a desired patient position and/or patient orientation) of the patient 22 with respect to the imaging hardware components associated with the imaging system 12 based on the signal indicative of the examination type received at block 84. For example, the database 14 may include one or more desired scan planes associated with different examination types corresponding to a particular anatomical feature, an imaging system, various characteristics of the patient (e.g., body type, height, weight, gender, age, or race) or a combination thereof. The controller 24 may receive data indicative of the scan planes from the database 14 based on the signal indicative of the examination type and determine the desired pose of the patient 22 to acquire the desired scan planes associated with the examination type. For example, the desired pose of the patient 22 may correspond to an optimal or an ideal pose of the patient 22 with respect to the imaging hardware components associated with the imaging system 12 to acquire the desired scan planes associated with the examination type.

At block 88, the controller 24 may provide a visualization of the desired pose of the patient 22 to acquire the desired scan planes associated with the examination type. In some embodiments, the visualization may include a 2D or a 3D graphic indicative of the desired position and/or orientation of the patient 22 based on the desired pose. For example, the visualization may provide a 2D or 3D graphic of the patient 22 in the desired pose such that the operator and/or the patient 22 may compare the current pose of the patient 22 to the desired pose via the display 30. The visualization of the desired pose of the patient 22 may be viewed simultaneously in the display 30 with the current pose of the patient 22.

At block 90, the controller 24 may determine whether the current pose of the patient 22 is correct. That is, the controller 24 may determine whether the current pose of the patient 22 is at the desired pose (e.g., the desired position and/or orientation) of the patient 22 with respect to the imaging hardware components of the imaging system 12 to acquire the desired scan planes of the patient 22. For example, the controller 24 may receive data indicative of a current position and/or orientation of the patient 22 from the patient position and/or orientations sensors 33.

In some embodiments, the controller 24 may determine whether the current pose of the patient 22 is correct by determining whether one or more anatomical reference points associated with the patient 22 or a patient pose mesh is within an acceptance region associated with the desired pose of the patient 22. The controller 24 may use deep learning techniques to establish the one or more anatomical reference points associated with the patient 22 or the patient pose mesh associated with the patient 22. For example, the controller 24 may receive image data associated with the patient 22 and use deep learning techniques to determine or identify one or more anatomical reference points associated with the patient 22 or a patient pose mesh associated with the patient 22 based on the image data. As described herein, the anatomical reference points may include the shoulders, the hips, the knees, or any other suitable anatomical landmark. The controller 24 may compare the anatomical reference points or the patient pose mesh determined from the image data of the patient 22 to the acceptance region associated with the desired pose of the patient 22 to determine whether the current pose of the patient 22 is at the desired position and/or orientation with respect to the imaging components of the imaging system 12. For example, the acceptance region may include one or more ranges associated with the desired position and/or orientation of the patient 22 with respect to the imaging components of the imaging system 12. If the anatomical reference points or the patient pose mesh is within the ranges associated with the desired position and/or orientation of the patient 22, the controller 24 may determine that the patient 22 is at the desired position and/or orientation to acquire the desired scan planes of the patient 22.

In other embodiments, the controller 24 may determine whether the current pose of the patient 22 is correct by determining whether one or more configuration variables associated with one or more expected internal anatomical features of the patient 22 is within acceptable ranges. For example, after generating the 3D surface map of the patient at block 72, the controller 24 may deform an anatomical atlas to the patient space defined by the 3D surface map of the patient 22. The anatomical atlas may include one or more anatomical models based on the examination type received at block 84. For example, if the examination type includes an X-ray of the patient's shoulder, the anatomical model may include anatomical models of the scapula, the clavicle, and the humerus. Each anatomical model may be associated with one or more configuration variables, such as the label index and name of the anatomical model in the database 14, component positions, component rotations, scaling factors, morphological factors, point correspondences between components, ranges of relative rotation, or joint-contact points. As such, the controller 24 may generate a set of configuration variables associated with expected internal anatomical features of the patient 22 after deforming the anatomical atlas to the patient pose defined by the 3D surface map of the patient 22. The controller 24 may compare each configuration variable in the set of configuration variables to the acceptable ranges associated with each configuration variable. For example, the acceptable ranges may include one or more ranges associated with the desired position and/or orientation of the patient 22 with respect to the imaging components of the imaging system 12. If each configuration variable is within a respective acceptable range, the controller 24 may determine that the patient 22 is at the desired position and/or orientation to acquire the desired scan planes of the patient 22.

If the controller 24 determines that the current pose of the patient 22 is at the desired position and/or orientation with respect to the imaging components of the imaging system 12 to acquire the desired scan planes of the patient 22, the controller 24 may begin image acquisition at block 96 according to the particular examination type received at block 84. For example, the controller 24 may send a command signal to the image acquisition hardware of the imaging system 12 to acquire the images of one or more desired anatomical features of the patient or one or more desired scan planes of the desired anatomical features of the patient 22. In some embodiments, the controller 24 may provide an indication that the current pose of the patient 22 is at the desired position and/or orientation. For example, the controller 24 may send a command signal to the display 30 to provide a visual indication (e.g., a graphic, a symbol, a green color) that the patient 22 is at the desired position and/or orientation. Similarly, the controller 24 may send a command signal to the display 30 to provide a visual indication (e.g., a graphic, a symbol, a red color) that the patient 22 is not at the desired position and/or orientation.

Alternatively, if the controller 24 determines that the current pose of the patient 22 is not at the desired position and/or orientation with respect to the imaging components of the imaging system 12, the controller 24 may provide guidance to the operator and/or the patient 22 to re-position the patient 22 at block 92. After the controller 24 provides guidance to the operator and/or the patient 22 to re-position the patient 22, the controller 24 may perform the method 60 of FIG. 3 at blocks 62 to 76, or any suitable combination thereof, at block 82. The controller 24 may generate a 3D surface map associated with the patient 22 and the patient's environment and generate a 3D patient model associated with the patient 22 based on the 3D surface map of the patient 22, a pose of the patient 22, and an anatomical atlas using the patient's current position and/or orientation. The controller 24 may compare the current position and/or orientation of the patient 22 to the desired pose (e.g., desired position and/or orientation) of the patient 22 with respect to the imaging hardware components of the imaging system 12. Based on the comparison of the current position and/or orientation of the patient 22 with the desired position and/or orientation of the patient 22, the controller 24 may determine a directional movement, an angular movement, or both, to assist the operator and/or the patient 22 in positioning and/or orienting the patient 22 in the desired position and/or orientation of the patient 22. The controller 24 may provide an indication of the directional movement, an angular movement, or both, to the operator and/or the patient 22 visually, audibly, haptically, or via any other suitable mechanisms to assist the operator in positioning and/or orienting the patient 22 in the desired patient position and/or orientation. For example, the controller 24 may direct the operator and/or patient 22 to position and/or orient the patient 22 in the desired pose such that the patient 22 aligns with a visualization of a 2D or 3D graphic of the patient 22 provided via the display 30. In another example, the controller 24 may send a command signal to one or more speakers to provide audible instructions to reposition the patient 22, or certain body parts of the patient 22. In some embodiments, the indication of the directional movement, the angular movement, or both, may be provided to the operator via an augmented reality device (e.g., augmented reality goggles or glasses, a smartphone, or a tablet), a projector that projects the indication directly onto the patient's skin, a haptic device (e.g., a probe, a glove, a phone, or a smartwatch), or the like.

After the patient 22 is repositioned in response to the guidance provided by the controller 24 at block 92, the controller 24 may repeat the determination of whether the current pose of the patient 22 is correct. As mentioned above, if the controller 24 determines that the current pose of the patient 22 is at the desired position and/or orientation with respect to the imaging components of the imaging system 12 to acquire the desired scan planes of the patient 22, the controller 24 may begin image acquisition at block 96 according to the particular examination type received at block 84. In some embodiments, the controller 24 may apply image segmentation to the 3D surface map generated at block 72 and generate the 3D patient model at block 76 before acquiring images of one or more desired anatomical features of the patient or one or more desired scan planes of the desired anatomical features of the patient 22 based on the examination type.

Figure 5:
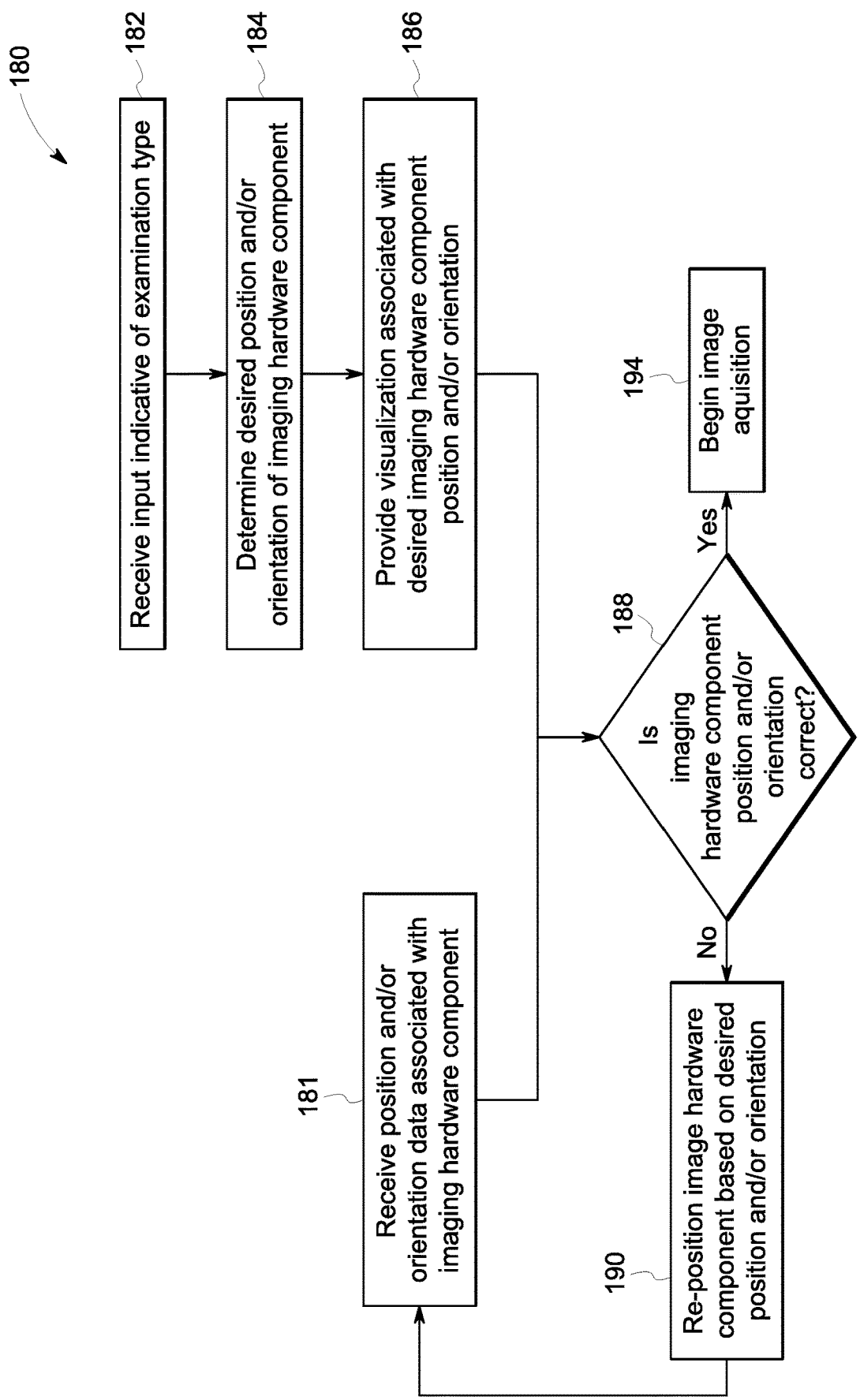
FIG. 5 is a flow chart of a method for positioning one or more imaging hardware components associated with an imaging system to acquire the desired scan plane of the desired anatomical feature of the patient of FIG. 1; in accordance with aspects of the present disclosure.

For certain imaging modalities, such as ultrasound imaging and X-ray imaging, the controller 24 may provide guidance to the operator to position one or more imaging hardware components of the imaging system 12 in a desired position and/or orientation to acquire one or more desired scan planes of one or more anatomical features of the patient 22. For example, the imaging hardware components may include an ultrasound probe or one or more X-ray detectors. With the foregoing in mind, FIG. 5 illustrates a flow chart of a method 180 for positioning the imaging hardware components of the imaging system 12 in the desired position and/or orientation to acquire the desired scan planes of the desired anatomical features of the patient 22. Although the following description of the method 180 is described in a particular order, it should be noted that the method 80 is not limited to the depicted order, and instead, the method 180 may be performed in any suitable order. Moreover, although the method 180 is described as being performed by the controller 24, it should be noted that it may be performed by any suitable computing device communicatively coupled to the controller 24.

Referring now to FIG. 5, at block 181, the controller 24 may receive position and/or orientation data associated with an imaging hardware component from a position sensor 36. In some embodiments, the position and/or orientation data associated with the imaging hardware component may be acquired in real-time or substantially real-time. At block 182, the operator may provide an examination type as an input for the controller 24 of the guidance system 10. As described above, the controller 24 may receive a signal (e.g., a user selection or a user input) indicative of the examination type associated with the patient 22 via one or more user input devices 28 or a database 14 communicatively coupled to the control unit 16. The examination type may include data indicative of one or more desired anatomical features of the patient 22 to be imaged or one or more desired scan planes to be acquired of the desired anatomical features of the patient 22. For example, the examination type may include data representative of a body part, a preliminary diagnosis of the patient 22, an imaging modality, or the like.

At block 184, the controller 24 may determine a desired imaging hardware component position and/or orientation based on the examination type received at block 182. For example, the database 14 may include one or more pre-defined imaging hardware component positions and/or orientations associated with different examination types corresponding to a particular anatomical feature, an imaging system, various characteristics of the patient (e.g., body type, height, weight, gender, age, or race), or a combination thereof. Based on the examination type received at block 182, the controller 24 may access the database 14 for the desired imaging hardware position and/or orientation that corresponds to the received examination type. For example, the desired imaging hardware position and/or orientation may correspond to an optimal or an ideal position and/or orientation associated with an imaging hardware component to acquire the desired scan planes associated with the examination type.

At block 186, the controller 24 may provide a visualization associated with the desired imaging hardware component and/or orientation. For example, the visualization may be indicative of a 2D or 3D graphic of the desired imaging hardware component position and/or orientation such that the operator may compare the current imaging hardware component position and/or orientation to the desired imaging hardware component position and/or orientation via the display 30. In some embodiments, the visualization may be viewed simultaneously in the display 30 with the current imaging hardware component position and/or orientation.

Based on a comparison of the current imaging hardware component position and/or orientation with the desired imaging hardware component position and/or orientation, the controller 24 of the guidance system 10 may automatically move or facilitate the manual placement of the corresponding imaging hardware component to the desired imaging hardware component position and/or orientation. For example, the controller 24 may send a command signal to one or more actuators to automatically position an X-ray detector in the desired position and/or orientation. In another example, the controller 24 may provide guidance to the operator to move an ultrasound probe to the appropriate position and/or orientation to acquire the desired scan plane of the desired anatomical feature of the patient 22. With the foregoing in mind, at block 188, the controller 24 may determine whether the current position and/or orientation of the imaging hardware component is correct. That is, the controller 24 may determine whether the current position and/or orientation of the imaging hardware component is at the desired position and/or orientation of the imaging hardware component to acquire the desired scan planes of the patient 22 according to the received examination types.

If the controller 24 determines that the current imaging hardware component position and/or orientation is at the desired imaging hardware component position and/or orientation, the controller 24 may begin image acquisition at block 96 according to the received examination type. In some embodiments, the controller 24 may provide an indication that the current imaging hardware component position and/or orientation is at the desired imaging hardware component position and/or orientation. For example, the controller 24 may send a command signal to the display 30 to provide a visual indication (e.g., a graphic, a symbol, a green color) that the imaging hardware component is at the desired position and/or orientation of the imaging hardware component. Similarly, the controller 24 may send a command signal to the display 30 to provide a visual indication (e.g., a graphic, a symbol, a red color) that the imaging hardware component is not at the desired position and/or orientation of the imaging hardware component.

Alternatively, if the controller 24 determines that the current imaging hardware component position and/or orientation is not at the desired position and/or orientation, the controller 24 may provide either automatically move the imaging hardware component to the desired position and/or orientation or provide guidance to the operator to manually position the imaging hardware component at the desired position and/or orientation at block 190. The controller 24 may compare the current position and/or orientation of the imaging hardware component to the desired position and/or orientation of the imaging hardware component to acquire the desired scan planes of the desired anatomical features of the patient 22. Based on the comparison of the current position and/or orientation of the imaging hardware component with the desired position and/or orientation of the imaging hardware component, the controller 24 may determine a directional movement, an angular movement, or both, to either automatically position the imaging hardware component in the desired position and/or orientation or assist the operator in manually positioning and/or orienting the imaging hardware component in the desired position and/or orientation of the patient 22. The controller 24 may provide an indication of the directional movement, an angular movement, or both, to the operator visually, audibly, haptically, or via any other suitable mechanisms to assist the operator in positioning and/or orienting the imaging hardware component in the desired position and/or orientation.

After the imaging hardware component is repositioned at block 190, the controller 24 may receive additional position and/or orientation data associated with the imaging hardware component from the position sensor 36, at block 181, and repeat the determination of whether the current imaging hardware component position and/or orientation is correct, at block 188. As mentioned above, if the controller 24 determines that the current position and/or orientation of the patient 22 is at the desired position and/or orientation to acquire the desired scan planes of the patient 22, the controller 24 may begin image acquisition at block 194 according to the particular examination type received at block 182.

In some embodiments, the controller 24 of the guidance system 10 may automatically determine and set one or more imaging parameters based on the anatomical model associated with the patient 22. For example, with regard to an ultrasound imaging system, after generating the anatomical model associated with the patient 22, the controller 24 of the guidance system 10 may determine the desired ultrasound probe position and/or orientation based on the desired scan plane to be acquired of the desired anatomical feature of the patient 22 or the desired examination type. Based on the desired ultrasound probe position and/or orientation with respect to the patient 22, the controller 24 of the guidance system 10 may automatically determine a depth setting associated with the ultrasound probe to focus the desired anatomy in the field of view of the ultrasound probe. The controller 24 may then send a command signal to the imaging system 12 to acquire ultrasound imaging data at the determined depth setting.

Additionally, the guidance system 10 may be configured to automatically adjust the imaging parameters during acquisition of imaging data and/or after acquiring imaging data. For example, with regard to the ultrasound probe described above, the depth setting may be adjusted after acquiring ultrasound imaging data of the patient 22 with the ultrasound probe. The controller 24 of the guidance system 10 may identify anatomical features within the ultrasound imaging data received from the imaging system 12, apply image segmentation to the ultrasound imaging data, and localize the identified anatomical features in the three-dimensional anatomical model associated with the patient 22 to generate an updated three-dimensional anatomical model. Based on the updated three-dimensional anatomical model, the controller 24 of the guidance system 10 may determine whether the current depth setting is appropriate to focus the desired anatomy in the field of view of the ultrasound probe. If the controller 24 of the guidance system 10 determines that the current depth setting is appropriate, the controller 24 may not send a signal to the imaging system 12 to change the depth setting and additional ultrasound imaging data may be acquired with the ultrasound probe at the current depth setting. If the controller 24 of the guidance system 10 determines that the current depth is not appropriate, the controller 24 may determine a new depth setting associated with the ultrasound probe to focus the desired anatomy in the field of view of the ultrasound probe. The controller 24 of the guidance system 10 may then send a command signal indicative of the new depth setting to the imaging system 12 to adjust the depth setting to the new depth setting and additional ultrasound imaging data may be acquired with the ultrasound probe at the new depth setting.

In another example, with regard to a CT imaging system, after generating the anatomical model associated with the patient 22, the controller 24 of the guidance system 10 may determine and adjust a desired radiation dose parameter and/or a desired machine-to-patient alignment (e.g., x-coordinate and y-coordinate with respect to anatomical model associated with the patient) to acquire imaging data of an anatomical feature of the patient 22. For instance, after generating the anatomical model associated with the patient 22, the imaging system 12 may acquire a two-dimensional (2D) topogram via a CT scanner and send the 2D topogram to the controller 24 of the guidance system 10. The controller 24 of the guidance system 10 may then identify anatomical features within the 2D topogram, apply image segmentation to the 2D topogram, and localize the identified anatomical features in the resulting three-dimensional anatomical model associated with the patient 22 to generate an updated three-dimensional anatomical model. Based on the updated three-dimensional anatomical model, the controller 24 of the guidance system 10 may determine whether the current radiation dose setting and/or the current machine-to-patient alignment are appropriate to properly image the anatomical feature of the patient 22. If the controller 24 of the guidance system 10 determines that the current radiation dose setting is appropriate, the controller 24 may not send a signal to the imaging system 12 to change the radiation dose setting and an additional 2D topogram may be acquired via the CT scanner at the current radiation dose setting. If the controller 24 of the guidance system 10 determines that the current radiation dose is not appropriate, the controller 24 may determine a new radiation dose setting associated with the CT scanner. The controller 24 may then send a signal indicative of the new radiation dose setting to the imaging system 12 to adjust the radiation dose setting to the new radiation dose setting and an additional 2D topogram may be acquired via the CT scanner at the new radiation dose setting. Additionally or alternatively, if the controller 24 determines that the current machine-to-patient alignment is appropriate, the controller 24 may send one or more command signals to the imaging system 12 to continue to acquire additional 2D topograms via the CT scanner at the current machine-to-patient alignment. If the controller 24 determines that the current machine-to-patient alignment is not appropriate, the controller 24 may determine a new machine-to-patient alignment associated with the CT scanner. The controller 24 may then send a command signal to the display 30 to output a visualization indicating the new machine-to-patient alignment to the patient 22 and/or the operator of the guidance system 10. After the patient 22 is re-positioned to the new machine-to-patient alignment with respect to the CT scanner, the controller 24 may send a command signal to the imaging system 12 to acquire an additional 2D topogram via the CT scanner.

In some embodiments, the controller 24 of the guidance system 10 may continuously or repeatedly adjust the imaging parameters of the imaging system 12 during acquisition of the imaging data and/or after acquiring the imaging data, thereby providing greater imaging precision and increasing an efficiency in image acquisition. Although automatic adjustment of imaging parameters is described herein with reference to a depth setting associated with an ultrasound probe, a radiation dose setting associated with a CT scanner, and a machine-to-patient alignment associated with the CT scanner, it should be noted that other imaging parameters may be automatically adjusted as described. For example, the imaging parameters may include the position and/or orientation of the patient 22 with respect to any imaging modality, the position and/or orientation of an imaging device with respect to the patient 22, a collimated x-ray cone projection (i.e., the projected area) associated with an x-ray imaging system, or any other suitable imaging parameters that upon adjustment may provide greater imaging precision or an increase in efficiency in image acquisition of the patient 22.

Although certain embodiments described herein involve the use of fixed-room based position and/or orientation sensors 33 (e.g., a stereo RGB-D camera mounted above the patient 22), it should be noted that other embodiments may be use a mobile device to acquire 3D surface map associated with the patient 22 and the patient's environment. In this way, the techniques described herein may provide a low-cost and mobile-based approach to providing guidance to the operator of the imaging system 12 via the mobile device to position and/or orient the patient 22 and/or the imaging hardware components associated with the imaging system 12 in respective positions and/or orientations to acquire a desired scan plane of a desired anatomical feature of the patient 22. In some embodiments, the techniques may also be used to provide guidance to the operator for non-imaging procedures and techniques, such as biopsies or venipuncture.

Figure 6:
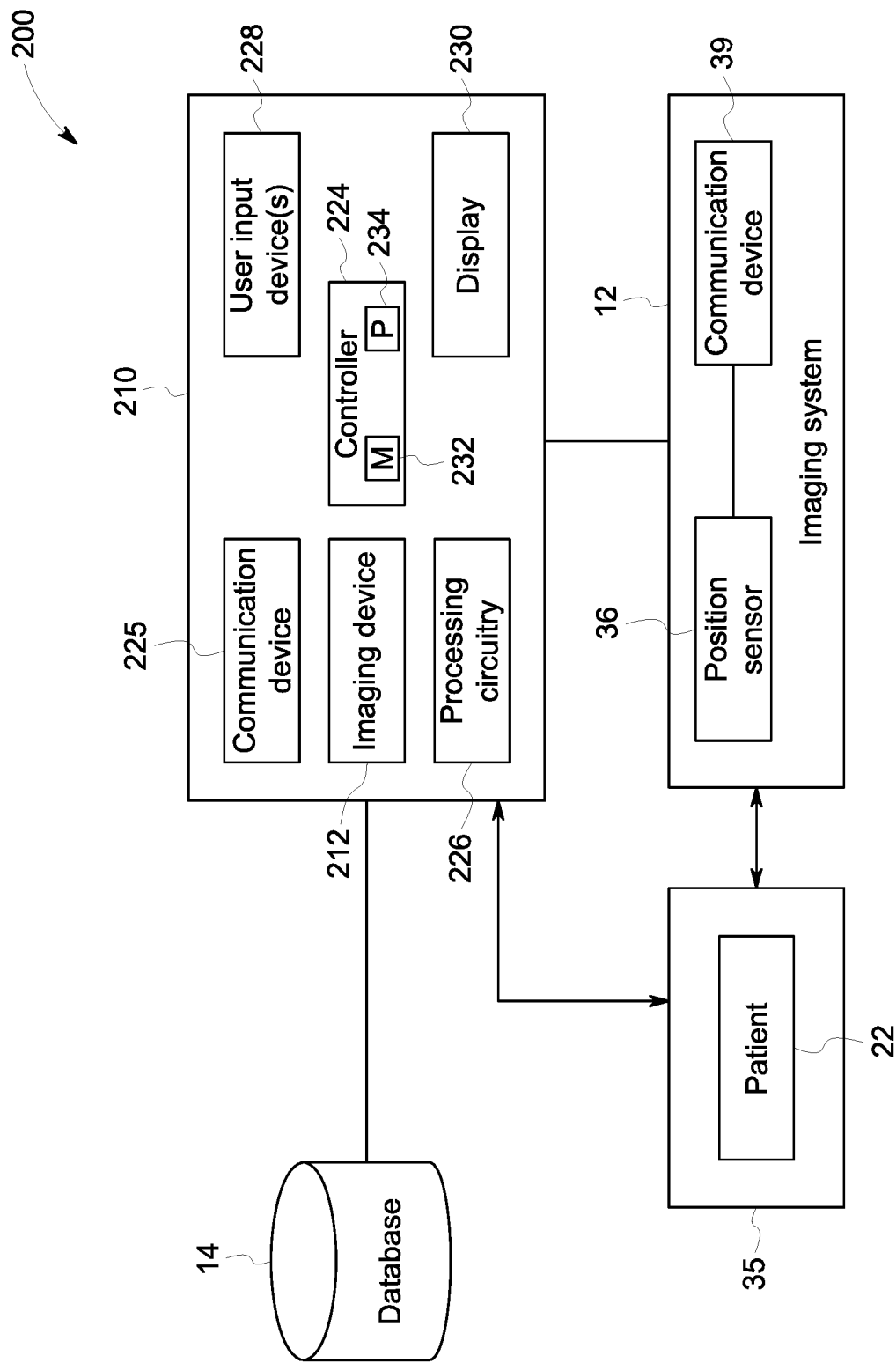
FIG. 6 illustrates a block diagram of an embodiment of a guidance system utilizing a mobile device to assist an operator in acquiring a desired scan plane of a desired anatomical feature of a patient, in accordance with aspects of the present disclosure.

With the foregoing in mind, FIG. 6 illustrates a block diagram of an embodiment of a mobile-based guidance system 200 having an imaging system 12 that may be used to acquire the desired scan plane of the desired anatomical features of the patient 22. In the illustrated embodiment, the guidance system 10 may include a mobile device 210 that may acquire image data of the patient 22 and the patient's environment in the patient space 35. The mobile device 210 may process the acquired image data and provide guidance to the operator to position and/or orient the patient 22, imaging hardware components associated with the imaging system 12, or both, via the mobile device 210. For example, the mobile device 210 may overlay certain expected anatomical features over an image or a video of the patient 22 displayed to the operator via the mobile device 210. In this way, the mobile device 210 may provide the operator with spatial awareness of the desired anatomical feature and/or the patient's anatomy adjacent to or surround the desired anatomical feature to facilitate proper imaging of the desired anatomical feature.

As described above, the imaging system 12 may include an ultrasound imaging system or any other suitable imaging modality that may be functionally compatible with the mobile device 210. The mobile device 210 may include augmented reality hand-held devices (e.g., a smartphone or a tablet), augmented reality head-mounted devices (e.g., goggles or glasses), a mobile, projection device, or any other suitable mobile device. The imaging system 12 may be communicatively coupled to the mobile device 210 via respective communication devices 35, 225. For example, the communication devices 35, 225 may communicate via one or more protocols such as various wired or wireless communication protocols, such as Wi-Fi, mobile telecommunications technology (e.g., 2G, 3G, 4G, or LTE), Bluetooth®, near-field-communications technology, and the like.

The mobile device 210 may include a controller 224, processing circuitry 226, one or more input devices 228, a display 230, and an imaging device 212. Similar to the controller 24 described above, the controller 224 may include a memory 232 and a processor 234. The controller 224 may control the imaging device 212 to acquire imaging data associated with the patient 22 and the patient's environment in the patient space 35. Additionally, the controller 224 may control other elements of the mobile device 210 to provide guidance to the operator of the imaging system 12 to acquire the desired scan plane of the desired anatomical feature of the patient 22. For example, the controller 224 may send a command signal to the display 230 to display an overlay of certain expected anatomical features over an image or a video of the patient 22 in the display 230.

Similar to the processing circuitry 26 described above, the processing circuitry 226 may include receiving and conversion circuitry. For example, the processing circuitry 226 may receive image data of the patient 22 and/or the patient's surroundings and process the image data, such as correcting for artifacts, or the like. The processing circuitry 226 may then generate an image or a series of images (e.g., a video) of the patient 22 for presentation via the display 230. The controller 224 may then cause display of the image or the series of images produced by the processing circuitry 226 via the display 230.

The controller 24 may receive a signal (e.g., a user selection or a user input) indicative of an examination type associated with the patient 22, a desired anatomical feature of the patient 22, a desired scan plane of the desired anatomical feature of the patient 22, or the like, via the user input devices 228. The user input devices 228 may include a touchscreen, a keyboard, buttons, or other devices suitable for allowing the operator to input a desired examination type, a desired anatomical feature, a desired scan plane, or the like.

As mentioned above, the controller 24 may provide visual guidance to the operator to position and/or orient the patient 22, the imaging hardware components, or both, via the mobile device 210. For example, the controller 224 may overlay certain anatomical features over an image or a video of the patient 22 displayed to the operator via the mobile device 210. By scanning the body of the patient 22 with the mobile device 210, the operator may generate a 3D surface map of the patient 22 and the patient's environment (e.g., a bed or a chair) and deform an anatomical atlas to the patient space 35 defined by the 3D surface map. For example, the anatomical atlas may be received from a database 14 communicatively coupled to the mobile device 210 over any suitable network.

With the foregoing in mind, FIG. 7 illustrates a series of visualizations 310, 320, 330, 340, 350, 360 of the patient 22 generated by the mobile device 230 and presented to the operator via the display 230 of the mobile device 210 to provide guidance to the operator to position an ultrasound probe 322 in a desired position and/or orientation to acquire ultrasound imaging data of the patient 22. Although the illustrated embodiment describes providing guidance to the operator to position the ultrasound probe 322 in the desired position and/or orientation, it should be understood that such techniques may be used to position other types of imaging hardware components or provide guidance to clinicians to perform non-imaging techniques as described herein. Additionally, in some embodiments, the mobile device 210 may generate a 3D patient model (e.g., an anatomical twin associated with the patient 22 and provide visual guidance to the operator using the same techniques or similar techniques as described above with respect to the controller 24. For example, as described herein, the mobile device 210 may generate the 3D patient model by generating a 3D surface map of the patient 22 and the patient's environment, identifying reference points within the 3D surface map, and deforming an anatomical atlas to the patient space defined by the 3D surface map of the patient 22 and/or the patient's environment.

As illustrated in the visualizations 310, 320, 330, 340, the operator may scan the body of the patient 22 with the imaging device 212 of the mobile device 210 to acquire 3D surface map of the patient 22 and the patient's surroundings. In the illustrated embodiment, the operator may scan the body of the patient 22 from the head of the patient 22 to the legs of the patient 22. However, it should be noted that in other embodiments, the operator may scan the body of the patient 22 in any other order (e.g., from the legs to the head or randomly) until a sufficient amount of 3D surface data of the patient 22 and the patient's surroundings is acquired. The mobile device 210 may provide indications of one or more surface points 312 of a plane to assist the operator in positioning and/or orienting the mobile device 210 to acquire the 3D surface map of the patient 22. Additionally, the mobile device 210 may provide indications of one or more 3D surface map points 314 in the visualizations 310, 320, 330, 340, 350 of the patient 22 to convey to the operator that the mobile device 210 has acquired a particular amount of 3D surface data associated with the patient 22. After the mobile device 210 has acquired a sufficient amount of 3D surface data associated with the patient 22 and the patient's surroundings, the mobile device 210 may provide an indication via the display 230 of the mobile device 210 to continue to the next step in the body scanning process. For example, the display 230 may change colors or provide a textual instruction for the operator to proceed to the next step. In some embodiments, the mobile device 210 may continue scanning the patient 22 and the patient's surroundings (e.g., acquiring 3D surface points) until the operator manually stops the scanning process. For example, mobile device 210 may present to the operator a touch input to stop scanning.

After the operator has finished scanning the body of the patient 22, the mobile device 210 may overlay certain anatomical features over an image or a video of the patient 22 presented to the operator via the display 230 of the mobile device 210. Similar to the process described above in FIG. 3, the mobile device 210 may determine or identify one or more anatomical reference points based on the 3D surface map associated with the patient 22 and the patient's environment. For example, the anatomical reference points may include the shoulders, the hips, the knees, or any other suitable anatomical landmark. The mobile device 210 may then estimate the current pose (e.g., the position and/or orientation) of the patient 22 based on the anatomical reference points and the 3D surface map using various keypoint techniques, mesh-based techniques, deep-learning techniques, or other suitable pose-estimation or pose-determination techniques. After estimating the current pose of the patient 22, the mobile device 210 may fuse the current pose of the patient 22 with the 3D surface map associated with the patient 22 and the patient's environment and extract one or more 3D anatomical reference points from the fused 3D surface map. The mobile device 210 may then generate a 3D surface map of the patient 22 and the patient's environment (e.g., a bed or a chair) based on the fused 3D surface map and register and deform one or more anatomical features from an anatomical atlas to the patient space defined by 3D surface map associated with the patient 22. In the illustrated embodiments, for example, the anatomical features may be presented as an overlay upon an image or a video of the patient 22. The anatomical features may include the heart 324, a fetus 326, or any other suitable anatomical features to provide the operator with spatial awareness of the expected positions of such features via the display 230 of the mobile device 210. In some embodiments, the types of anatomical features overlaid upon the image or the video of the patient 22 may be based on an examination type input received from the operator.

Additionally, the mobile device 210 may provide guidance to the operator to move one or more imaging hardware components of the imaging system 12 to acquire a desired scan plane of a desired anatomical feature of the patient 22. Similar to the embodiments described above (e.g., in FIG. 5), the mobile device 210 may determine a desired position and/or orientation 322 of the ultrasound probe to acquire a desired scan plane of a desired anatomical feature of the patient 22. For example, the mobile device 210 may determine a desired position and/or orientation 322 of the ultrasound probe that may be used by the operator to image the patient 22. In some embodiments, the desired position and/or orientation 322 of the ultrasound probe may be represented to the user as a visualization (e.g., a virtual reality visualization or an augmented reality visualization) via the mobile device. As described above, the imaging system 12 may include one or more position sensors 36 for detecting the position and/or orientation of respective imaging hardware components of imaging system 12. The position sensor 36 may be communicatively coupled to the controller 224 of the mobile device 210 via a wired or wireless connection and may send one or more signals to the controller 224 of the mobile device indicative of the current position and/or orientation of the imaging hardware component.

In some embodiments, the mobile device 210 and the position sensors 36 of the imaging system 12 may develop a common coordinate system to provide guidance to the operator. For example, the mobile device 210 may use computer vision to localize the imaging hardware via pattern matching of a known 3D shape of the imaging hardware with RGB-D data from the mobile device 210 or generated 3D surface data, attachment of optical markers on a probe and localization of these markers to infer a larger rigid body of the imaging hardware, a fiducial placed in the patient space such that the position sensors 36 of the imaging system 12 may localize relative to the fiducial and the mobile device may collect 3D surface data or 2D images of the fiducial when collecting the 3D surface map to co-localize with the fiducial. In another example, a fixed dock may be implemented that either the mobile device 210 or imaging hardware of the imaging system 12 fit into, or a dock for the mobile device 210 may be integrated as part of the imaging system 12 such that the coordinate systems of both the mobile device 210 and the imaging system 12 are unified.

In any case, the controller 224 of the mobile device 210 may receive the current position and/or orientation of the ultrasound probe. The controller 224 may compare the current position and/or orientation of the ultrasound probe 322 to the desired position and/or orientation 322 of the ultrasound probe. Based on the comparison, the controller 224 may determine whether the ultrasound probe 322 is in the desired position and/or orientation 322 to sufficiently image the desired anatomical feature of the patient 22. If the controller 224 determines that the ultrasound probe is not in the desired position and/or orientation 322, the controller 224 may provide guidance to the operator to move the ultrasound probe the desired position and/or orientation 322. For example, the controller 224 may direct the operator to move (or not move) the ultrasound probe in a combination of directions and/or angles to position the ultrasound probe to the desired position and/or orientation 322 to acquire the desired scan plane of the desired anatomical feature of the patient 22.

In some embodiments, the controller 224 of the mobile device 210 may determine one or more directional movements, one or more angular movements, or both, to position the ultrasound probe in the desired position and/or orientation 322. The controller 224 may then provide an indication of the direction movements, the angular movements, or both, to the operator visually, audibly, haptically, or via any other suitable mechanisms to assist the operator in positioning and/or orienting the ultrasound probe 322 in the desired position and/or orientation. After the ultrasound probe 322 is repositioned, the controller 224 may repeat the determination of whether the current position and/or orientation of the ultrasound probe is correct and provide further guidance to the operator if the current position and/or orientation of the ultrasound probe is determined not to be correct.

Technical effects of the invention include providing guided imaging techniques to an operator of a medical imaging system to acquire one or more desired scan planes of one or more desired anatomical features of a patient. For example, based on a respective imaging modality (e.g., ultrasound, MRI, CT, X-ray), the guidance system may assist the operator in positioning and/or orienting one or more imaging hardware components associated with the imaging modality, the patient with respect to the imaging hardware components, or both, to acquire the desired scan planes of the desired anatomical features of the patient. In some embodiments, the guidance system may assist the operator via a 3D patient model that visually presents the expected position and/or orientation of anatomical features of the patient to the operator.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging guidance system, comprising:
  a patient sensor configured to receive three-dimensional (3D) data associated with a patient;
  an imaging system comprising an imaging hardware component configured to acquire image data of an anatomical feature associated with the patient, wherein the imaging system comprises a hardware position sensor associated with the imaging hardware component; and
  a processor configured to:
    generate a 3D surface map associated with the patient based on the 3D data;
    generate a 3D patient space from the 3D surface map associated with the patient;
    generate a 3D patient model by mapping an anatomical atlas to the 3D patient space, wherein the 3D patient model comprises one or more 3D representations of anatomical features of a human body within the 3D patient space;
    determine a desired position associated with the imaging hardware component to acquire image data of the anatomical feature;
    determine a current position associated with the imaging hardware component from the hardware position sensor; and
    determine a desired movement associated with the imaging hardware component to position the imaging hardware component at the desired position.

2. The medical image guidance system of claim 1, wherein the processor is configured to receive the anatomical atlas from a database based on one or more patient characteristics associated with the patient, wherein the patient characteristics comprise a height of the patient, a weight of the patient, a gender of the patient, an ethnicity of the patient, or any combination thereof.

3. The medical image guidance system of claim 1, wherein the anatomical atlas is at least partially generated based on medical imaging data associated with the patient.

4. The medical image guidance system of claim 1, wherein the patient sensor comprises a red-green-blue-depth (RGB-D) camera, a stereo RGB-D camera, a depth-sensing camera, a radar scanning system, or a laser scanning system.

5. The medical image guidance system of claim 1, wherein the patient sensor comprises the hardware position sensor and the hardware position sensor has integrated position tracking, wherein the patient sensor is configured to receive the 3D data by acquiring 3D surface points associated with the patient.

6. The medical imaging guidance system of claim 1, wherein the patient sensor is integrated in a mobile device, and wherein the mobile device and the hardware position sensor of the imaging system are associated with a common coordinate system.

7. The medical imaging guidance system of claim 1, wherein the hardware position sensor comprises an accelorometer, a gyroscope, an inertial measurement unit, an electromagnetic tracking sensor, an optical tracking sensor, or any other suitable sensor.

8. The medical image guidance system of claim 1, comprising providing an indication of the desired movement associated with the imaging hardware component to position the imaging hardware component at the desired position, wherein the indication of the desired movement comprises one or more directional movements, one or more angular movements, or both, associated with the imaging hardware component.

9. A method, comprising:
generating a three-dimensional (3D) surface map associated with a patient from a patient sensor;
generating a 3D patient space from the 3D surface map associated with the patient;
determining a current pose associated with the patient based on the 3D surface map associated with the patient;
comparing the current pose with a desired pose associated with the patient with respect to an imaging system, wherein the desired pose facilitates imaging of an anatomical feature of the patient by the imaging system;
determining a recommended movement based on the comparison between the current pose and the desired pose, wherein the recommended movement is configured to reposition the patient in the desired pose; and
providing an indication of the recommended movement.

10. The method of claim 9, comprising providing a visualization of the desired pose via a display, wherein the visualization comprises a graphical representation of the desired pose.

11. The method of claim 9, wherein the indication is provided via an augmented reality device.

12. The method of claim 9, comprising:
generating an additional 3D surface map associated with the patient from the patient sensor;
determining an additional current pose associated with the patient based on the additional 3D surface map;
determining that the additional current pose is at the desired pose based on a comparison between the additional current pose and the desired pose; and
providing an indication that the patient is in the desired pose.

13. The method of claim 12, comprising generating a 3D patient model by applying an anatomical atlas to the 3D patient space, wherein the 3D patient model comprises one or more 3D representations of anatomical features of a human body within the 3D patient space.

14. A medical imaging guidance system, comprising:
a processor configured to:
generate a three-dimensional (3D) surface map associated with a patient from a patient sensor;
generate a 3D patient space from the 3D surface map associated with the patient;
generate a 3D patient model by applying an anatomical atlas to the 3D patient space, wherein the 3D patient model comprises one or more 3D representations of anatomical features of a human body within the 3D patient space; and
determine a desired position associated with an imaging hardware component of an imaging system configured to acquire image data of the anatomical feature.

15. The medical imaging guidance system of claim 14, wherein the patient sensor is a mobile device.

16. The medical imaging guidance system of claim 14, wherein the processor is configured to extract 3D anatomical landmarks by identifying two-dimensional (2D) anatomical reference points based on 2D sensor data and fuse the 2D anatomical reference points with the 3D surface map.

17. The medical imaging guidance system of claim 14, wherein applying the anatomical atlas to the 3D patient space comprises identifying a 3D patient surface in the 3D surface map and registering the anatomical atlas with the 3D patient surface.

18. The medical imaging guidance system of claim 17, wherein registering the anatomical atlas with the 3D patient surface comprises registering the anatomical atlas with the 3D patient surface using a rigid transformation, an affine transformation, or a deformable transformation.

19. The medical imaging guidance system of claim 14, wherein applying the anatomical atlas to the 3D patient space comprises identifying 3D anatomical landmarks based on the 3D surface map, looking up corresponding 3D anatomical landmarks in the anatomical atlas, and generating the 3D patient model by performing a rigid, affine, or deformable transformation to map anatomy from the anatomical atlas into the 3D patient space.

20. The medical imaging guidance system of claim 14, wherein applying the anatomical atlas to the 3D patient space comprises performing a piece-wise rigid, affine, or deformable transformation of sections of the anatomical atlas to corresponding sections of the 3D patient space to perform a mapping from a 3D pose of the anatomical atlas into a complex 3D pose of the 3D patient model, wherein the sections are defined by a connectivity map of adjacent 3D patient landmarks, segments of the 3D surface map associated with the patient, or a combination thereof.

* * * * *